US011058760B2

(12) United States Patent
Flanegan et al.

(10) Patent No.: US 11,058,760 B2

(45) Date of Patent: Jul. 13, 2021

(54) N-ANTIGENIC FORM POLIOVIRUS VIRUS-LIKE PARTICLES COMPRISING THERMOSTABLE MUTATIONS

(71) Applicant: University of Florida Research Foundation, Incorporated, Gainesville, FL (US)

(72) Inventors: James B. Flanegan, Gainesville, FL (US); Robert McKenna, Gainesville, FL (US); Christopher Daniel Boone, College Station, TX (US); Sushma Abraham Ogram, Gainesville, FL (US); Barbara Joan Morasco, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/094,504

(22) PCT Filed: Apr. 18, 2017

(86) PCT No.: PCT/US2017/028210

§ 371 (c)(1),
(2) Date: Oct. 18, 2018

(87) PCT Pub. No.: WO2017/184655

PCT Pub. Date: Oct. 26, 2017

(65) Prior Publication Data

US 2019/0117763 A1 Apr. 25, 2019

Related U.S. Application Data

(60) Provisional application No. 62/324,252, filed on Apr. 18, 2016.

(51) Int. Cl.

| | |
|---|---|
| ***A61K 39/13*** | (2006.01) |
| ***C07K 14/005*** | (2006.01) |
| ***A61K 39/12*** | (2006.01) |
| ***C12N 7/00*** | (2006.01) |
| ***C07K 14/105*** | (2006.01) |
| ***A61P 31/14*** | (2006.01) |
| *A61K 39/00* | (2006.01) |

(52) U.S. Cl.

CPC .............. *A61K 39/13* (2013.01); *A61K 39/12* (2013.01); *A61P 31/14* (2018.01); *C07K 14/005* (2013.01); *C07K 14/105* (2013.01); *C12N 7/00* (2013.01); *A61K 2039/5258* (2013.01); *C12N 2770/32622* (2013.01); *C12N 2770/32623* (2013.01); *C12N 2770/32634* (2013.01); *C12N 2770/32651* (2013.01); *Y02A 50/30* (2018.01)

(58) Field of Classification Search

CPC .................. A61K 39/13; C07K 14/105; C12N 2770/32634; C12N 2770/32623; C12N 2770/32622

See application file for complete search history.

(56) References Cited

U.S. PATENT DOCUMENTS

| | | | | |
|---|---|---|---|---|
| 2007/0160628 | A1 | 7/2007 | Birkett et al. | |
| 2014/0356962 | A1 | 12/2014 | Wimmer et al. | |
| 2015/0030620 | A1 | 1/2015 | Bachmann et al. | |
| 2015/0056244 | A1 * | 2/2015 | Cardosa ................... | C12N 7/00 424/196.11 |
| 2015/0374812 | A1 | 12/2015 | Karpilow et al. | |

FOREIGN PATENT DOCUMENTS

WO WO 2018/134584 7/2018

OTHER PUBLICATIONS

Vignuzzi, M., et al., Jan. 2006, Quasispecies diversity determines pathogenesis through cooperative interactions in a viral population, Nature 439:344-348.*

Nguyen, Y., et al., Mar. 2019, Identification and characterization of a poliovirus capsid mutant with enhanced thermal stability, J. Virol. 93(6):e01510-18 (pp. 1-11).*

Fox, H., et al., Jan. 2017, Genetically thermo-stabilised, immunogenic poliovirus empty capsids; a strategy for non-replicating vaccines, PLoS Pathogens 13(1):e1006117 (pp. 1-14).*

Shiomi, H., et al., 2004, Isolation and characterisation of poliovirus mutants resistant to heating at 50 degrees C for 30 min, J. Med. Virol. 74:484-491.*

Colston, E., and V. R. Racaniello, 1994, Soluble receptor-resistant poliovirus mutants identify surface and internal capsid residues that control interaction with the cell receptor, EMBO J. 13(24):5855-5862.*

Fox, H., et al., Jan. 2017, Genetically thermo-stabilised, immunogenic poliovirus empty capsids; a strategy for non-replicating vaccines, PLoS Pathog. 13(1):e1006117, pp. 1-14.*

Adeyemi, O. O., et al., Feb. 2017, Increasing type 1 poliovirus capsid stability by thermal selection, J. Virol. 91 (4):e01586-16, pp. 1-17 (published online Dec. 7, 2016).*

International Search Report and Written Opinion for Application No. PCT/US2017/028210 dated Jul. 27, 2017.

International Preliminary Report on Patentability for Application No. PCT/US2017/028210 dated Nov. 1, 2018.

Adeyemi et al., Increasing Type 1 Poliovirus Capsid Stability by Thermal Selection. J Virol. Jan. 31, 2017;91(4). pii: e01586-16. doi: 10.1128/JVI.01586-16. Print Feb. 15, 2017.

(Continued)

*Primary Examiner* — Jeffrey S Parkin

(74) *Attorney, Agent, or Firm* — Wolf, Greenfield & Sacks, P.C.

(57) ABSTRACT

Provided herein are compositions of virus like particles (VLPs) of poliovirus (PV) that have one or more stabilizing mutations that confer a higher degree of thermostability to the N-antigenic form of the VLPs. These VLPs are non-infectious, and thus safer for use in vaccine development and administration to clinical subjects.

18 Claims, 10 Drawing Sheets

Specification includes a Sequence Listing.

(56) References Cited

OTHER PUBLICATIONS

Albrecht et al., Poliovirus and polio antibody assay in HEp-2 and Vero cell cultures. J Biol Stand. Apr. 1983;11(2):91-7.
Barton et al., Assays for poliovirus polymerase, 3D(Pol), and authentic RNA replication in HeLa S10 extracts. Methods Enzymol. 1996;275:35-57.
Basavappa et al., Role and mechanism of the maturation cleavage of VPO in poliovirus assembly: structure of the empty capsid assembly intermediate at 2.9 A resolution. Protein Sci. Oct. 1994;3(10):1651-69.
Bräutigam et al., Formation of poliovirus-like particles by recombinant baculoviruses expressing the individual VPO, VP3, and VP1 proteins by comparison to particles derived from the expressed poliovirus polyprotein. Virology. Feb. 1993;192(2):512-24.
Chung et al., Enterovirus 71 virus-like particle vaccine: improved production conditions for enhanced yield. Vaccine. Oct. 8, 2010;28(43):6951-7. doi: 10.1016/j.vaccine.2010.08.052. Epub Aug. 24, 2010.
Colston et al., Soluble receptor-resistant poliovirus mutants identify surface and internal capsid residues that control interaction with the cell receptor. EMBO J. Dec. 15, 1994;13(24):5855-62.
Duggal et al., Genetic recombination of poliovirus in a cell-free system. Proc Natl Acad Sci U S A. Dec. 9, 1997;94(25):13786-91.
Fox et al., Genetically Thermo-Stabilised, Immunogenic Poliovirus Empty Capsids; a Strategy for Non-replicating Vaccines. PLoS Pathog. Jan. 19, 2017;13(1):e1006117. doi: 10.1371/journal.ppat.1006117. eCollection Jan. 2017.
Franco et al., Stimulation of poliovirus synthesis in a HeLa cell-free in vitro translation-RNA replication system by viral protein 3CDpro. J Virol. May 2005;79(10):6358-67.
Icenogle et al., A neutralizing monoclonal antibody against poliovirus and its reaction with related antigens. Virology. Nov. 1981;115(1):211-5.
Ku et al., A virus-like particle based bivalent vaccine confers dual protection against enterovirus 71 and coxsackievirus A16 infections in mice. Vaccine. Jul. 23, 2014;32(34):4296-303. doi: 10.1016/j.vaccine.2014.06.025. Epub Jun. 17, 2014.
Lane et al., Production, purification, crystallization and preliminary X-ray analysis of adeno-associated virus serotype 8. Acta Crystallogr Sect F Struct Biol Cryst Commun. Jun. 1, 2005;61(Pt 6):558-61. Epub Jun. 1, 2005.
Li et al., Virus-like particles for enterovirus 71 produced from *Saccharomyces cerevisiae* potently elicits protective immune responses in mice. Vaccine. Jul. 11, 2013;31(32):3281-7. doi: 10.1016/j.vaccine.2013.05.019. Epub May 29, 2013.
Liu et al., Characterization of enterovirus 71 capsids using subunit protein-specific polyclonal antibodies. J Virol Methods. Jan. 2013;187(1):127-31. doi: 10.1016/j.jviromet.2012.09.024. Epub Oct. 6, 2012.
Macadam et al., Rational design of genetically stable, live-attenuated poliovirus vaccines of all three serotypes: relevance to poliomyelitis eradication. J Virol. Sep. 2006;80(17):8653-63.
Molla et al., Cell-free, de novo synthesis of poliovirus. Science. Dec. 13, 1991;254(5038):1647-51.
Ojala et al., Identification of discrete polyadenylate-containing RNA components transcribed from HeLa cell mitochondrial DNA. Proc Natl Acad Sci U S A. Feb. 1974;71(2):563-7.
Porta et al., Rational engineering of recombinant picornavirus capsids to produce safe, protective vaccine antigen. PLoS Pathog. Mar. 2013;9(3):e1003255. doi: 10.1371/journal.ppat.1003255. Epub Mar. 27, 2013.
Rombaut et al., A pH-dependent dissociation of poliovirus procapsids. Virology. Mar. 1987;157(1):245-7.
Rombaut et al., Denaturation of poliovirus procapsids. Arch Virol. 1989;106(3-4):213-20.
Rombaut et al Immunogenic, non-infectious polio subviral particles synthesized in *Saccharomyces cerevisiae*. J Gen Virol. Aug. 1997;78 ( Pt 8):1829-32.
Shiomi et al., Isolation and characterisation of poliovirus mutants resistant to heating at 50 degrees Celsius for 30 min. J Med Virol. Nov. 2004;74(3):484-91.
Tang et al., Poliovirus RNA recombination in cell-free extracts. RNA. Jun. 1997;3(6):624-33.
Thompson et al., Critical assessment of influenza VLP production in Sf9 and HEK293 expression systems. BMC Biotechnol. May 16, 2015;15:31. doi: 10.1186/s12896-015-0152-x.
Vincente et al., Large-scale production and purification of VLP-based vaccines. J Invertebr Pathol. Jul. 2011;107 Suppl:S42-8. doi: 10.1016/j.jip.2011.05.004.
Watson et al., Leukemia viruses associated with mouse myeloma cells. Proc Natl Acad Sci U S A. Jun. 1970;66(2):344-51.
Xiao et al., Large-scale production of foot-and-mouth disease virus (serotype Asia1) VLP vaccine in *Escherichia coli* and protection potency evaluation in cattle. BMC Biotechnol. Jul. 2, 2016;16(1):56. doi: 10.1186/s12896-016-0285-6.
Yakovenko et al., Antigenic evolution of vaccine-derived polioviruses: changes in individual epitopes and relative stability of the overall immunological properties. J Virol. Mar. 2006;80(6):2641-53.

* cited by examiner

N-ANTIGENIC FORM POLIOVIRUS VIRUS-LIKE PARTICLES COMPRISING THERMOSTABLE MUTATIONS

RELATED APPLICATIONS

This application is a national stage filing under 35 U.S.C. § 371 of international application number PCT/US2017/028210, filed on Apr. 18, 2017, and claims the benefit under 35 U.S.C. § 119(e) of U.S. Provisional Patent Application No. 62/324,252, filed on Apr. 18, 2016, entitled "Stable Poliovirus Variants And Uses Thereof," the entire contents of each of which are incorporated by reference herein.

BACKGROUND

The incidence of poliovirus (PV) infection has been reduced by the use of current vaccines, the oral polio vaccine (OPV) and the inactivated polio vaccine (IPV). However, the vaccine strain in the OPV can, in some recipients, revert to a virulent form that is capable of causing vaccine-associated paralytic polio (VAPP). IPV cannot be used on a worldwide basis because infectious virus is handled in its manufacture, which renders it expensive to produce. Thus, there is a need to develop safer and more affordable inactivated PV vaccines (IPVs) or non-infectious PV vaccines to eradicate PV globally.

SUMMARY

In some aspects, the disclosure provides a composition comprising poliovirus (PV) virus like particles (VLPs) comprising one or more stabilizing mutations, wherein the VLPs are thermostable in N-antigenic form.

In some embodiments, the poliovirus is poliovirus serotype 1 (PV1). In some embodiments, the poliovirus is poliovirus serotype 2 (PV2). In some embodiments, the poliovirus is poliovirus serotype 3 (PV3). In some embodiments, the composition comprises one or more of PV1, PV2, and PV3.

In some embodiments, the VLPs sediment at 74S on a 15-30% sucrose gradient.

In some embodiments, the VLPs are 20-40 nm in diameter. In some embodiments, the VLPs are 30 nm in diameter.

In some embodiments, the VLPs are at a titer of 1-10 N-antigenic units/W. In some embodiments, the VLPs are at a titer of 0.1-100 N-antigenic units/W.

In some embodiments, the one or more stabilizing mutations are at positions selected from the list consisting of: VP3(178Q), VP3(202L), VP3(167V), VP3(4V), VP1(147N), VP1(231A), and VP2(201R). In some embodiments, the one or more stabilizing mutations are selected from the list consisting of: VP3(178Q.L), VP3(202L.E), VP3(167V.D), VP3(4V.C), VP1(147N.C), VP1(231A.V), and VP2(201R.K).

In some embodiments, the PV is PV1 and the one or more stabilizing mutations are at positions selected from the list consisting of: VP3(178Q), VP3(202L), VP3(167V), VP3(4V), VP1(147N), VP1(231A), and VP2(201R). In some embodiments, the PV is PV1 and the one or more stabilizing mutations are selected from the list consisting of: VP3(178Q.L), VP3(202L.E), VP3(167V.D), VP3(4V.C), VP1(147N.C), VP1(231A.V), and VP2(201R.K).

In some embodiments, the PV is PV2 and the one or more stabilizing mutations are at a position selected from the list consisting of: VP3(178Q), VP3(202L), VP3(167V), VP3(4V), VP1(147N), VP1(231A), and VP2(201R). In some embodiments, the PV is PV2 and the one or more stabilizing mutations are selected from the list consisting of: VP3(178Q.L), VP3(202L.E), VP3(167V.D), VP3(4V.C), VP1(147N.C), VP1(231A.V), and VP2(201R.K).

In some embodiments, the PV is PV3 and the one or more stabilizing mutations are at positions selected from the list consisting of: VP3(178Q), VP3(180T) and VP3(236D). In some embodiments, the PV is PV3 and the one or more stabilizing mutations are selected from the list consisting of: VP3(178Q.L), VP3(180T.V) and VP3(236D.V).

In some embodiments, one or more of the amino acid substitutions described for any of the PV described in this application can be replaced with a conservative amino acid substitution. For example, a polar, a non-polar, a charged, a hydrophobic, a hydrophilic, an acidic, a basic, a neutral, etc., amino acid substitution can be replaced respectively with a corresponding polar, non-polar, charged, hydrophobic, hydrophilic, acidic, basic, neutral, etc., amino acid substitution.

In some embodiments, one or more stabilizing mutations are at the interface between one or more VP proteins in the VLP. In some embodiments, one or more stabilizing mutations are at positions 1-10 amino acids upstream of VP3(178Q), or 1-10 amino acids downstream of VP3(178Q). In some embodiments, the one more stabilizing mutations are at positions of VP3 that interface with VP1.

In some embodiments, the VLPs are thermostable in N-antigenic form for up to 8 h at 37° C. In some embodiments, the VLPs are thermostable in N-antigenic form for up to 48 h at 37° C. In some embodiments, the VLPs are thermostable in N-antigenic form for up to 5 days at 37° C. In some embodiments, the VLPs are thermostable in N-antigenic form for up to 8 h at 39° C. In some embodiments, the VLPs are thermostable in N-antigenic form for up to 48 h at 39° C. In some embodiments, the VLPs are thermostable in N-antigenic form for up to 5 days at 39° C.

In some aspects, the disclosure provides a poliovirus vaccine comprising one or more of the poliovirus VLP compositions described in this application.

In some embodiments, the poliovirus vaccine is bivalent. In some embodiments, the poliovirus vaccine is trivalent.

In some aspects, the disclosure provides a method comprising administering a dose of a therapeutically effective amount of a poliovirus vaccine comprising a variant poliovirus VLP to a subject in need thereof.

In some aspects, the disclosure provides a method of producing any one of the PV VLPs disclosed herein. In some embodiments, a method of producing any one of the PV VLPs disclosed herein comprises running a cell-free reaction at a temperature of around 30° C. In some embodiments, the cell-free reaction comprises a HeLa cell extract.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1A illustrates the formation of N-form VLPs, or empty capsids, of wildtype PV VLPs and their subsequent conversion to H-form empty capsids. FIG.

1B illustrates the formation of stable N-form VLPs, of PV VLPs comprising stabilizing mutations.

Figure 2:
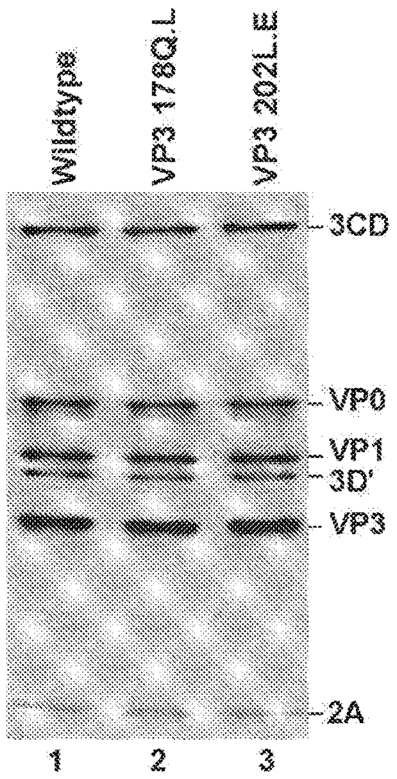

FIG. 2 shows translation of PV1 wildtype, VP3(178Q.L) and VP3(202L.E) expression RNAs in HeLa S10 cell-free reactions. The expression RNAs were translated in the presence of [$^{35}$S]methionine and the resulting labeled proteins were analyzed by SDS-PAGE.

Figure 3A:
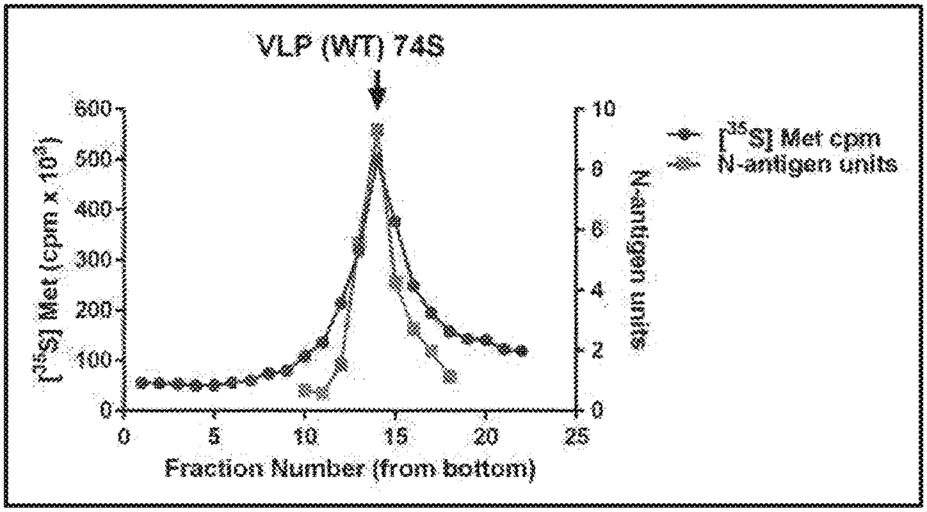
Figure 3B:
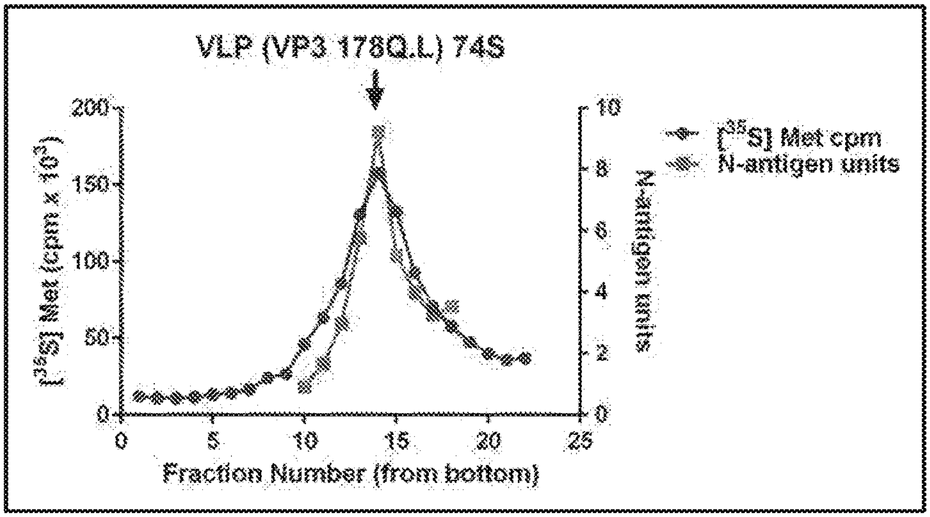

FIG. 3A and FIG. 3B illustrate the sedimentation of labeled wild type and PV1 VP3(178Q.L) VLPs in a 15-30% sucrose gradient, respectively. VLPs were synthesized in HeLa cell-free translation reactions in the presence of [$^{35}$S] methionine and fractionated on a 15-30% sucrose gradient. The radioactivity of a portion of each fraction was determined by trichloroacetic acid (TCA) precipitation. The peak fractions of wildtype PV1 or PV1VP3 (178Q.L) VLPs are shown. The N-antigenic units of the peak fractions were determined by ELISA. The peak of radioactivity and N-antigenic units are coincident for both the wildtype and VP3 (178Q.L) VLPs.

Figure 4:
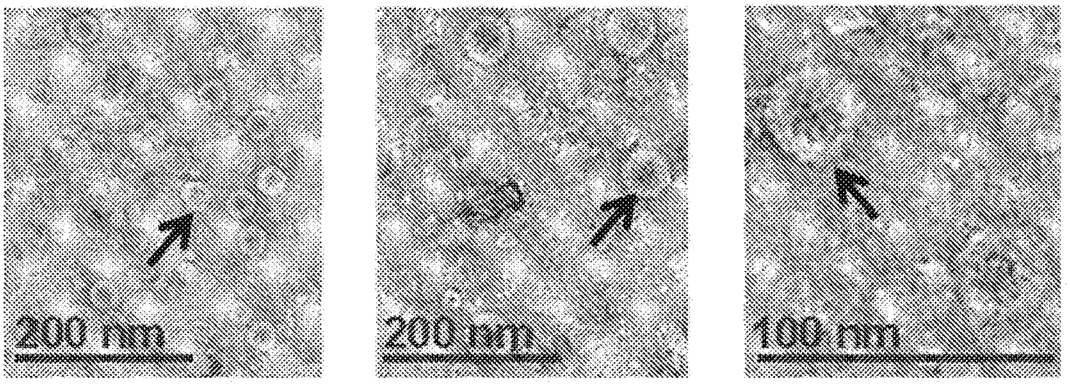

FIG. 4 shows transmission electron micrographs of PV1 VP3(178Q.L) VLPs. VLPs were synthesized in HeLa cell-free reactions and were sedimented on a 15-30% sucrose gradient. The 74S peak fractions were identified by ELISA. Pooled peak fractions were pelleted by ultracentrifugation and a portion of the resuspended pellet was visualized by transmission electron microscopy (TEM). The magnification of the left image is 15,000×, middle image is 26,000×, and the right image is 52,000×. Single VLPs were found to be approximately 30 nm in diameter.

Figure 5:
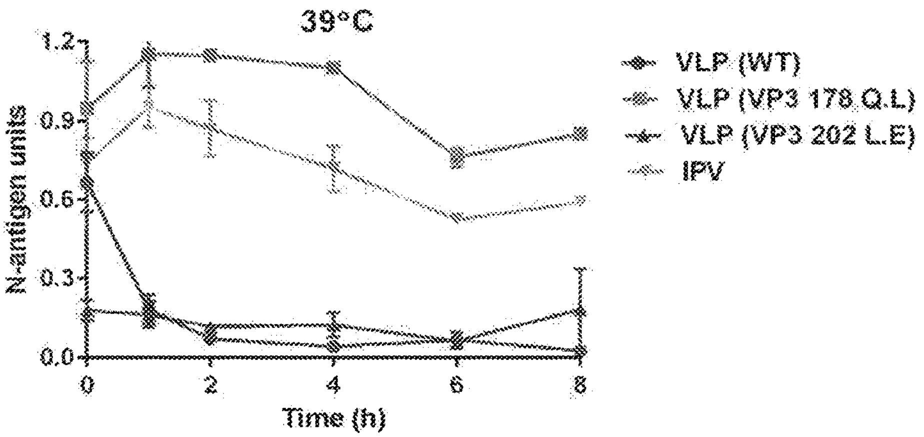

FIG. 5 shows the thermo stability of N-antigenic form of wildtype and mutant PV1 VLPs during an 8h incubation at 39° C. Inactivated poliovirus (IPV) was used as a control. Aliquots were removed at the indicated time points, and the N-antigenic units in each sample were determined by ELISA.

Figure 6:
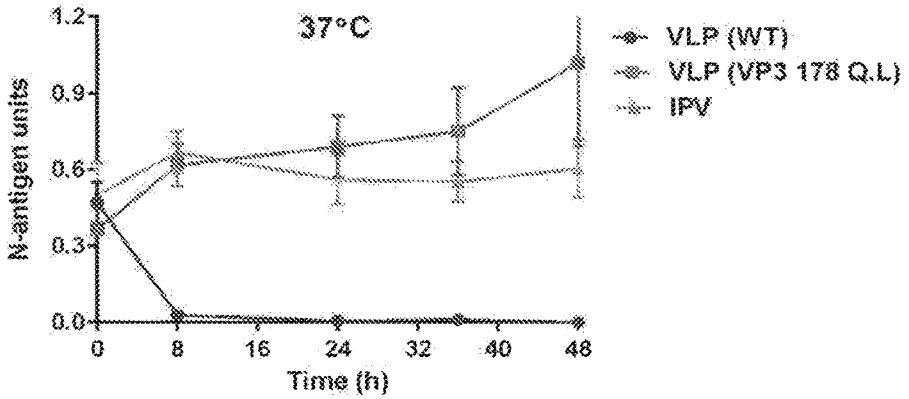
Figure 6:
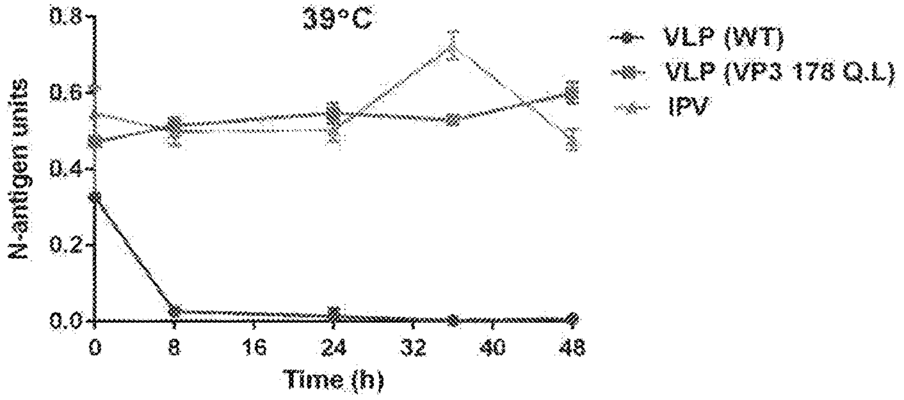

FIG. 6 shows the thermostability of N-antigenic form of wildtype and PV1 VP3(178Q.L) mutant VLPs during a 48h incubation at 37° C. (top panel) and 39° C. (bottom panel). Inactivated poliovirus (IPV) was used as a control. Aliquots were removed at the indicated time points, and the N-antigenic units in each sample were determined by ELISA.

Figure 7:
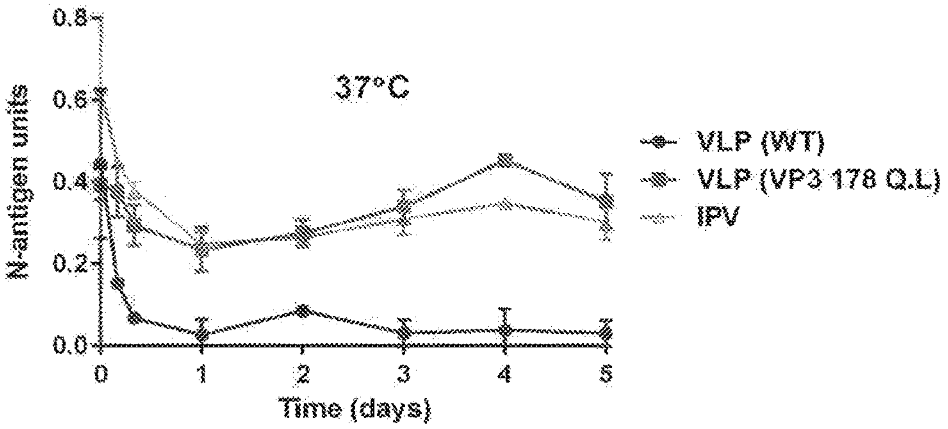

FIG. 7 shows the thermostability of N-antigenic form of wildtype and PV1 VP3(178Q.L) mutant VLPs during a 5 day incubation at 37° C. Inactivated poliovirus (IPV) was used as a control. Aliquots were removed at the indicated time points, and the N-antigenic units in each sample were determined by ELISA.

Figure 8:
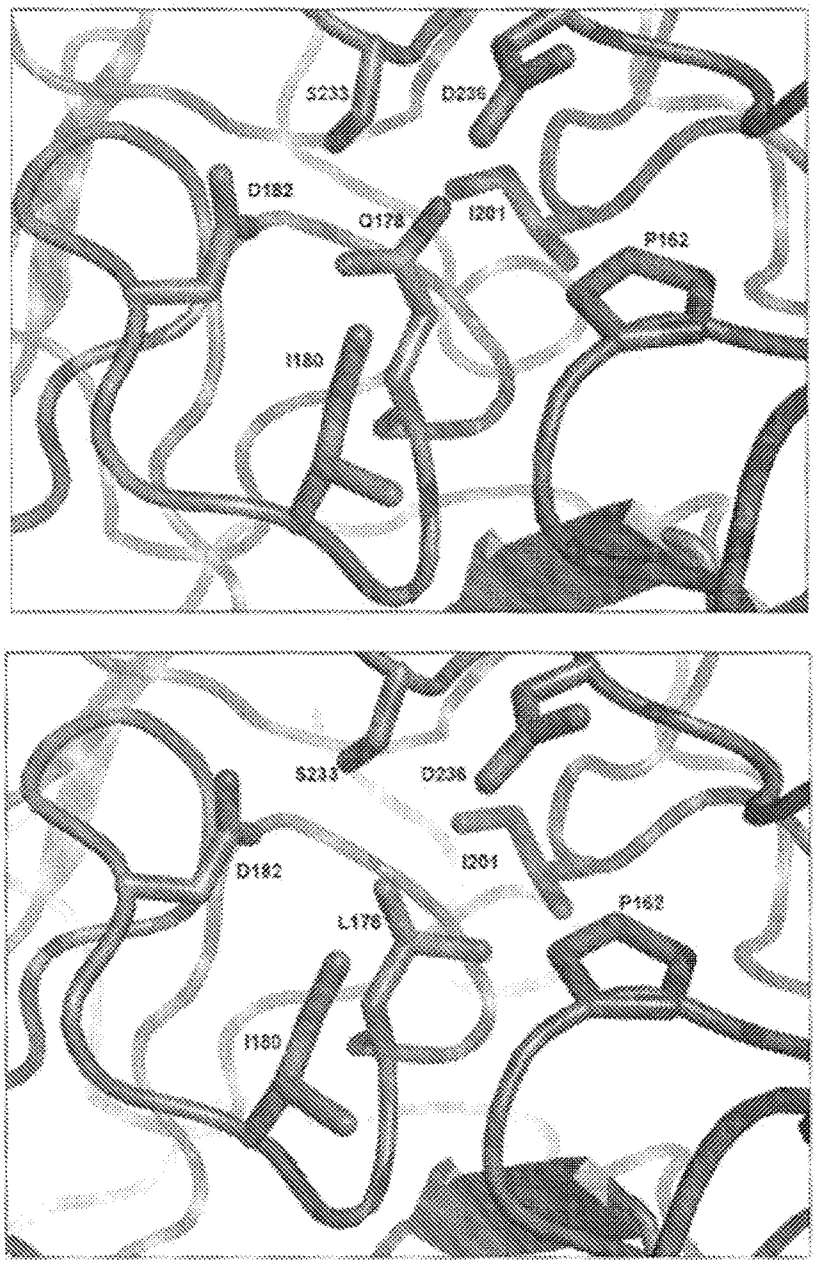

FIG. 8 depicts in silico modeling of PV1 capsid interfaces. VP3 (amino acids in the bottom left corner of the images) and VP1 (amino acids in the top right corner of the images) interface of wildtype (top image) and VP3(Q178.L) capsid (bottom image) interfaces are shown. Reference PDB ID: 1HXS.

Figure 9:
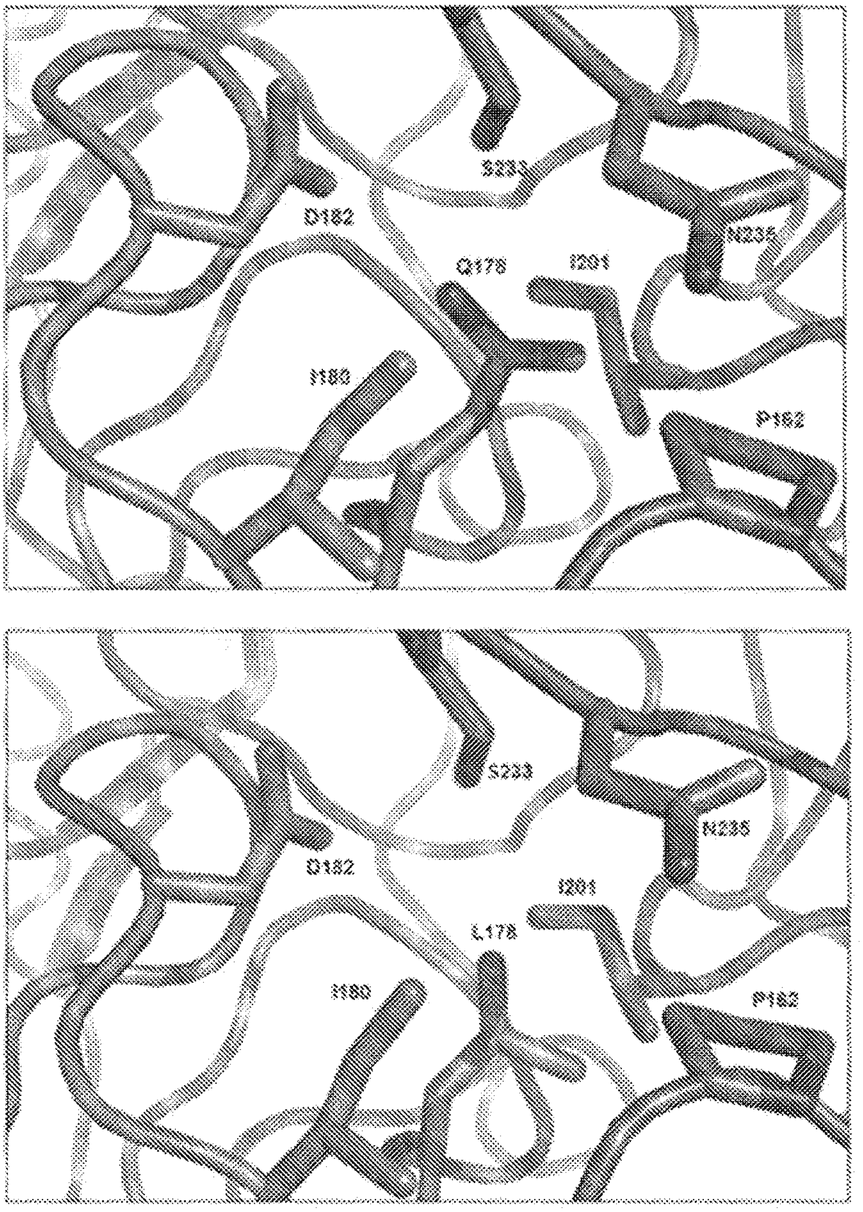

FIG. 9 depicts in silico modeling of PV2 capsid interfaces. VP3 (amino acids in the bottom left corner of the images) and VP1 (amino acids in the top right corner of the images) interface of wildtype (top image) and VP3(Q178.L) capsid (bottom image) interfaces are shown. Reference PDB ID: 1EAH.

Figure 10:
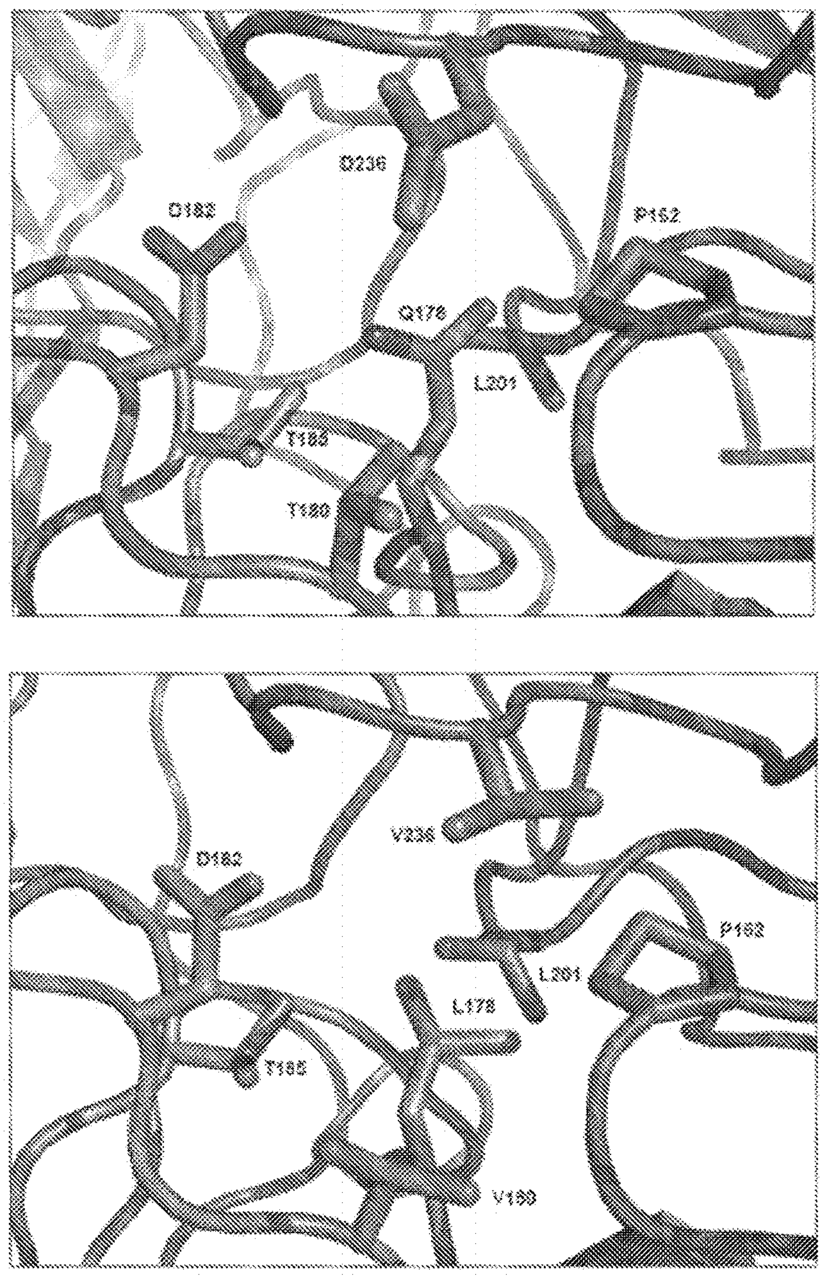

FIG. 10 depicts in silico modeling of PV3 capsid interfaces. VP3 (amino acids in the bottom left corner of the images) and VP1 (amino acids in the top right corner of the images) interface of wildtype (top image) and VP3(Q178.L) capsid (bottom image) interfaces are shown. Reference PDB ID: 1PVC.

DETAILED DESCRIPTION

The two vaccines currently used against poliovirus are the oral polio vaccine (OPV) and the inactivated polio vaccine (IPV). Their use has been tremendously helpful in reducing the number of new polio cases worldwide. However, the continued transmission of poliovirus in a few countries is a major challenge and continues to pose a risk for outbreaks in the polio-free countries of the world. To this end, the Global Polio Eradication Initiative (GPEI) and the WHO have initiated an 'End-Game Strategy' and a poliovirus eradication campaign.

A major drawback of using OPV is the ability of the vaccine strain to revert to a virulent form that is capable of causing vaccine-associated paralytic polio (VAPP) in some vaccine recipients and their contacts. Due to this problem, developed countries now exclusively use the IPV. Unfortunately, IPV cannot be used on a worldwide basis as it is expensive to produce and administer. Wildtype virus is used as the seed virus for the production of IPV, which results in major containment and safety issues at production facilities to ensure that wildtype virus is not released to the general population. This increases the cost of the vaccine and limits the construction of new vaccine production facilities. These issues make it important to develop new vaccines without the shortcomings of the present day vaccines for eradication to succeed in the long term. Therefore, there is an urgent need to develop new vaccines without the limitations of the present day vaccines for eradication to succeed in the long term. In particular, the development of a new inactivated vaccine from a non-pathogenic strain or, even better, a non-infectious virus-like particle (VLP) is a high priority. The current strategies being developed to engineer non-pathogenic strains employ mutagenesis of the genomic RNA to debilitate the virus. Vaccines made using this strategy, however, will still use infectious seed virus that has the potential to revert or recombine to generate pathogenic virus if there was an accidental release of the attenuated virus.

As described in this application, useful inactivated poliovirus vaccine will maintain the stability and immunogenicity of the wildtype virus capsid but be incapable of producing infectious virus. In this case, new vaccine production facilities could be built in developing countries resulting in a significant reduction in the cost of producing and transporting the vaccine to places of need.

The development of non-infectious virus-like particle (VLP) vaccine has the potential to fulfil the requirements for improved inactivated PV vaccine. In some embodiments, VLPs for use in vaccine compositions maintain the thermostability and immunogenicity of the wildtype virus, but are also incapable of producing infectious virus. Such VLPs would allow vaccine production facilities to be built in developing countries resulting in a significant reduction in the cost of vaccine production. Development of a noninfectious vaccine is of strategic importance to the global polio eradication initiative (GPEI) and the polio end-game strategy.

By definition, VLPs are virus capsids that are empty of nucleic acid, or capsids that do not carry any RNA for replication. For PV, the challenge is to produce stable forms of VLPs, known as N-forms of VLPs that confer an antigenic surface that will produce an immunogenic response when administered to clinical subjects. Herein, "stable" or "stability" refers to "thermostable" antigenic forms or "thermostability" of antigenic forms. Herein the "N-form" or "N-antigenic form" of VLPs or IPV refers to a forms of VLPs or IPV that confer antigenic sites on the surface, which in turn are responsible for producing an immune response in subjects. "N-form" or "N-antigenic form" are used interchangeably. Herein, a stable VLP refers to the stable N-form VLP.

Poliovirus native empty capsids (74S) do not contain any viral RNA and are composed of 60 copies of the proteins, VP0, VP1 and VP3. The precursor protein, P1, is cleaved by 3CD protease into VP0, VP3 and VP1, which readily assemble into the 74S empty capsids. These native or wildtype empty capsids are antigenically identical to mature virus in that they are in the N antigenic form when they are initially made in cells (Icenogle J, et al., Virology 115:211-215, 1981). However, when the N-form of the native empty capsid is exposed to physiological temperatures, it undergoes a conformational change and is converted to the H-(heat-denatured-) form (Rombaut, B. et al., Virology 157: 245-247, 1987; Rombaut, B. et al., Arch. Virol. 106:213-220, 1989). The N-antigenic form of the native or wildtype empty capsid closely mimics wildtype virus and produces an immunogenic response, which includes the production of neutralizing antibodies. Therefore, the native empty capsids in the N-form are VLPs that have the potential to be used as a non-infectious vaccine. Recombinant empty capsids or VLPs can be produced by minimally expressing the P1 precursor protein and the 3CD viral protease. The challenge is to stabilize the VLPs such that they remain in the N-form and do not undergo the conformational change to the H-form.

These problems are addressed by the disclosed PV VLPs that were developed using a rational mutagenic approach. Herein are disclosed compositions of PV VLPs comprising stabilizing mutations that confer a higher degree of thermostability to the N-antigenic form of the VLP. The disclosed compositions are useful as new mono-valent, bi-valent, or tri-valent non-infectious PV VLP vaccines.

In some aspects, a composition comprising PV VLPs having one or more stabilizing mutations is provided, wherein the VLPs are thermostable in N-antigenic form. The antigenic form of PV VLPs is one which confers an antigenic surface that produces a high titer of neutralized antibodies when injected into a subject.

There are three serotypes of poliovirus. In some embodiments, the poliovirus is of serotype 1 (PV1). In some embodiments, the poliovirus is of serotype 2 (PV2). In some embodiments, the poliovirus is of serotype 3 (PV3). In some embodiments, a composition comprises poliovirus of serotype 1(PV1) and of serotype 2 (PV2). In some embodiments, a composition comprises poliovirus of serotype 1 (PV1) and of serotype 3 (PV3). In some embodiments, a composition comprises poliovirus of serotype 2 (PV2) and serotype 3(PV3). In some embodiments, a composition comprises poliovirus of serotype 1 (PV1), serotype 2 (PV2), and serotype 3(PV3). In some embodiments, VLPs comprise proteins belonging to more than one PV serotype.

In some embodiments, the VLPs of the disclosed composition sediment at 74S on a 15-30% sucrose gradient.

In some embodiments, the VLPs of the disclosed PV VLPs are of 30 nm diameter. In some embodiments, the VLPs of the disclosed PV VLPs are of a diameter in the range of 28-32 nm. However, it should be appreciated that VLPs of other sizes, e.g., those having a diameter in the range of 25-35 nm, or 20-40 nm may be made and used.

In some embodiments, the stabilizing mutation that confers a higher degree of stability to the mutant VLPs compared to wildtype VLPs is at one of the following positons: VP3(178Q), VP3(202L), VP3(167V), VP3(4V), VP1 (147N), VP1(231A), and VP2(201R). In some embodiments, the stabilizing mutation that confers a higher degree of stability to the mutant VLPs compared to wildtype VLPs is VP3(178Q.L). Herein, VP3(178Q.L) and Q178L are equivalent and represent a substitution of a leucine for a glutamine at position 178. Equivalent notations are used for other mutants described in this application.

In some embodiments, the stabilizing mutation that confers a higher degree of stability to the mutant VLPs compared to wildtype VLPs is VP3(167V.D). In some embodiments, the stabilizing mutation that confers a higher degree of stability to the mutant VLPs compared to wildtype VLPs is VP3(4V.C). In some embodiments, the stabilizing mutation that confers a higher degree of stability to the mutant VLPs compared to wildtype VLPs is VP1(147N.C). In some embodiments, the stabilizing mutation that confers a higher degree of stability to the mutant VLPs compared to wildtype VLPs is VP1(231A.V). In some embodiments, the stabilizing mutation that confers a higher degree of stability to the mutant VLPs compared to wildtype VLPs is VP2(201R.K).

In some embodiments, the stabilizing mutation that confers a higher degree of stability to the PV3 mutant VLPs compared to wildtype PV3 VLPs is at one or more of the following positions: VP3(178Q.L), VP3(180T.V) and VP3 (236D.V). In some embodiments, the stabilizing mutation that confers a higher degree of stability to the PV3 mutant VLPs compared to wildtype PV3 VLPs is VP3(178Q.L). In some embodiments, the stabilizing mutation that confers a higher degree of stability to the PV3 mutant VLPs compared to wildtype PV3 VLPs is VP3(180T.V). In some embodiments, the stabilizing mutation that confers a higher degree of stability to the PV3 mutant VLPs compared to wildtype PV3 VLPs is VP3(236D.V).

In some embodiments, a VP3(202L.E) may be prepared and used, however it should be noted that VP3(202L.E) mutation is not as effective as the VP3(178Q.L) or WT VPS (see e.g., Table 2).

In some embodiments, the stabilizing mutation that confers a higher degree of stability to the mutant VLPs compared to wildtype VLPs is at a position, or amino acid, that is at the interface between one or more VP proteins in the VLP. In some embodiments, the stabilizing mutation that confers a higher degree of stability to the mutant VLPs compared to wildtype VLPs is at a position, or amino acid, that interface between VP0 and VP1. In some embodiments, the stabilizing mutation that confers a higher degree of stability to the mutant VLPs compared to wildtype VLPs is at a position, or amino acid, that is part of the interface between VP0 and VP3. In some embodiments, the stabilizing mutation that confers a higher degree of stability to the mutant VLPs compared to wildtype VLPs is at a position, or amino acid, that is part of the interface between VP1 and VP3. In some embodiments, the stabilizing mutation that confers a higher degree of stability to the mutant VLPs compared to wildtype VLPs are at positons of VP3 that interface with VP1. Herein, "position" is used interchangeably with "amino acid".

In some embodiments, the stabilizing mutation is one that provides a hydrogen bond interaction or van der Waals contact patch with surrounding amino acids that stabilizes the N-form of the VLP. In some embodiments, the stabilizing mutation is one that allows hydrogen bond interaction or van der Waals interactions in neighboring or surrounding amino acids without hydrogen bond interaction or van der Waals interactions with the mutated amino acid directly. In some embodiments, the stabilizing mutation is at a position 1-10 amino acids upstream of VP3(178Q), or 1-10 amino acids downstream of VP3(178Q). In some embodiments, the stabilizing mutation is at a position the side chain of which is in the vicinity of 0.5-20 angstroms (for example, 1-5, or 5-10, 10-20 angstroms) from VP3(178Q). In some embodiments, the stabilizing mutations is at a position the side chain of which is in the vicinity of 0.5-5 angstroms from VP3(178Q). In some embodiments, the stabilizing mutation is at a position the side chain of which is in the vicinity of 5-10 angstroms from VP3(178Q).

It is to be understood that more than one stabilizing mutations (e.g., 2, 3, 4, 5, or more of the mutations described in this application) can be designed into a VLP to improve the thermostability of its N-form.

In some embodiments, the VLPs of the disclosed compositions are thermostable in the N-antigenic form for up to 4 hours at physiological temperatures. In some embodiments, the VLPs of the disclosed compositions are thermostable in the N-antigenic form for up to 8 hours at physiological temperatures. In some embodiments, the VLPs of the disclosed compositions are thermostable in the N-antigenic form for up to 24 hours at physiological temperatures. In some embodiments, the VLPs of the disclosed compositions are thermostable in the N-antigenic form for up to 48 hours at physiological temperatures. In some embodiments, the VLPs of the disclosed compositions are thermostable in the N-antigenic form for up to 5 days at physiological temperatures. In some embodiments, the VLPs of the disclosed compositions are thermostable in the N-antigenic form for up to 10 days at physiological temperatures. In some embodiments, the VLPs of the disclosed compositions are thermostable in the N-antigenic form for up to 30 days at physiological temperatures. In some embodiments, the VLPs of the disclosed compositions are thermostable in the N-antigenic form for up to 90 days, or longer (e.g., 90-900 days), at physiological temperatures.

In some embodiments, the VLPs of the disclosed compositions are thermostable in the N-antigenic form for up to 4 hours at 37° C. In some embodiments, the VLPs of the disclosed compositions are thermostable in the N-antigenic form for up to 8 hours at 37° C. In some embodiments, the VLPs of the disclosed compositions are thermostable in the N-antigenic form for up to 24 hours at 37° C. In some embodiments, the VLPs of the disclosed compositions are thermostable in the N-antigenic form for up to 48 hours at 37° C. In some embodiments, the VLPs of the disclosed compositions are thermostable in the N-antigenic form for up to 5 days at 37° C. In some embodiments, the VLPs of the disclosed compositions are thermostable in the N-antigenic form for up to 10 days at 37° C. In some embodiments, the VLPs of the disclosed compositions are thermostable in the N-antigenic form for up to 30 days at 37° C. In some embodiments, the VLPs of the disclosed compositions are thermostable in the N-antigenic form for up to 90 days, or longer (e.g., 90-900 days), at 37° C.

In some embodiments, the VLPs of the disclosed compositions are thermostable in the N-antigenic form for up to 4 hours at 39° C. In some embodiments, the VLPs of the disclosed compositions are thermostable in the N-antigenic form for up to 8 hours at 39° C. In some embodiments, the VLPs of the disclosed compositions are thermostable in the N-antigenic form for up to 24 hours at 39° C. In some embodiments, the VLPs of the disclosed compositions are thermostable in the N-antigenic form for up to 48 hours at 39° C. In some embodiments, the VLPs of the disclosed compositions are thermostable in the N-antigenic form for up to 5 days at 39° C. In some embodiments, the VLPs of the disclosed compositions are thermostable in the N-antigenic form for up to 10 days at 39° C. In some embodiments, the VLPs of the disclosed compositions are thermostable in the N-antigenic form for up to 30 days at 39° C. In some embodiments, the VLPs of the disclosed compositions are thermostable in the N-antigenic form for up to 90 days, or longer (e.g., 90-900 days), at 39° C.

In some embodiments, the VLPs of the disclosed compositions are thermostable in the N-antigenic form for up to 4 hours at a temperature up to 40° C. In some embodiments, the VLPs of the disclosed compositions are thermostable in the N-antigenic form for up to 8 hours at a temperature up to 40° C. In some embodiments, the VLPs of the disclosed compositions are thermostable in the N-antigenic form for up to 24 hours at a temperature up to 40° C. In some embodiments, the VLPs of the disclosed compositions are thermostable in the N-antigenic form for up to 48 hours at a temperature up to 40° C. In some embodiments, the VLPs of the disclosed compositions are thermostable in the N-antigenic form for up to 5 days at a temperature up to 40° C. In some embodiments, the VLPs of the disclosed compositions are thermostable in the N-antigenic form for up to 10 days at a temperature up to 40° C. In some embodiments, the VLPs of the disclosed compositions are thermostable in the N-antigenic form for up to 30 days at a temperature up to 40° C. In some embodiments, the VLPs of the disclosed compositions are thermostable in the N-antigenic form for up to 90 days, or longer (e.g., 90-900 days), at a temperature up to 40° C.

In some embodiments, the VLPs of the disclosed compositions are thermostable in the N-antigenic form for up to 4 hours at a temperature up to 50° C. In some embodiments, the VLPs of the disclosed compositions are thermostable in the N-antigenic form for up to 8 hours at a temperature up to 50° C. In some embodiments, the VLPs of the disclosed compositions are thermostable in the N-antigenic form for up to 24 hours at a temperature up to 50° C. In some embodiments, the VLPs of the disclosed compositions are thermostable in the N-antigenic form for up to 48 hours at a temperature up to 50° C. In some embodiments, the VLPs of the disclosed compositions are thermostable in the N-antigenic form for up to 5 days at a temperature up to 50° C. In some embodiments, the VLPs of the disclosed compositions are thermostable in the N-antigenic form for up to 10 days at a temperature up to 50° C. In some embodiments, the VLPs of the disclosed compositions are thermostable in the N-antigenic form for up to 30 days at a temperature up to 50° C. In some embodiments, the VLPs of the disclosed compositions are thermostable in the N-antigenic form for up to 90 days, or longer (e.g., 90-900 days), at a temperature up to 50° C.

In some embodiments, the VLPs of the disclosed compositions show a thermostability that is equivalent to the antigenic thermostability of PV1 IPV. In some embodiments, the VLPs of the disclosed compositions show a thermostability that is equivalent to the antigenic thermostability of PV2 IPV. In some embodiments, the VLPs of the disclosed compositions show a thermostability that is equivalent to the antigenic thermostability of PV3 IPV. By "equivalent to the antigenic thermostability", it is meant that the thermostability of IPV under various or different conditions is similar.

In some aspects, a poliovirus vaccine is disclosed, wherein the vaccine comprises one or more disclosed compositions of mutant VLPs. In some embodiments, the poliovirus vaccine is monovalent. In some embodiments, the poliovirus vaccine is bivalent. In some embodiments, the poliovirus vaccine is trivalent.

In some embodiments, a vaccine comprising the disclosed N-form VLPs do not require the use of live virus for their production, and thus provide a less expensive option of PV vaccine production. Moreover, they will be an affordable IPV that can be used worldwide in the pre- and post-eradication era. Disclosed VLP comprising vaccines may therefore replace both OPV and IPV that are used currently. Stable N-form PV1, PV2 and PV3 VLPs that are immunogenic and produce high-titer neutralizing antibodies will represent a major advancement toward development of monovalent, bivalent, and trivalent VLP vaccines.

In some embodiments, a composition comprising a poliovirus vaccine as disclosed herein is sterile. In some embodiments, a composition comprising a PV vaccine comprises a pharmaceutically acceptable carrier, e.g., including a buffer and/or a salt that stabilize the vaccine and/or the composition comprising the vaccine. In some embodiments, a composition comprising a PV vaccine comprises an adjuvant that increases the immune reaction to the vaccine. Examples of adjuvants are aluminum and monophosphoryl lipid A.

In some aspects, a method comprising administering a dose of a therapeutically effective amount of a poliovirus vaccine to a subject in need thereof is disclosed. In some embodiments, "administering" or "administration" means providing a material to a subject in a manner that is pharmacologically useful. In exemplary embodiments, a poliovirus vaccine comprising VLPs as described herein can be administered to a subject (e.g., a mammalian subject, such as a human subject). In some embodiments, the poliovirus vaccine is administered to humans, for example human patients. In some embodiments, the subjects is a mammal. In some embodiments, the mammal is a non-human primate, mouse, rat, pig, horse, dog, cat, guinea pig, or other mammal.

In some embodiments, a vaccine composition comprises one or more poliovirus VLPs and one or more adjuvants. In some embodiments, vaccine compositions comprise any adjuvant(s) that can be used to activate an immune response in a subject. In some embodiments, an adjuvant can be any substance or any compound incorporated into a vaccine composition that increases the immune response of a subject to a poliovirus VLP preparation described herein. Examples of adjuvants include, but are not limited to, poly-ICLC, Poly (I:C), GM-CSF, BCG, monophosphoryl lipid A, MF59, Freund's adjuvants, Montanide IMS, Montanide ISA 206, Montanide ISA-51, Montanide ISA 50V, Aluminium salts, Alhydrogel, Rehydrogel HPA, PLGA, MPL1, AS04, AS01B, AS02A, P3CSK4, CpG-ODN, Imiquimod ISS, ONTAK, LipoVac, Amplivax, CpG7909, dSLIM, IC30, IC31, SRL172, virus particles, YF-17D, AS15, OK-432, IMP321, OM-174, cytokines, and/or other adjuvants, for example adjuvants that are used with current poliovirus vaccines.

In some embodiments, vaccines are administered separately from one or more adjuvant(s). In some embodiments, vaccines are administered along with one or more adjuvant(s). In some embodiments, vaccine compositions comprise one or more adjuvants and one or more VLP preparations.

In some embodiments, vaccine compositions comprise different carriers such as polysaccharides, polypeptides, proteins, liposomes, or antigen presenting cells. In some embodiments, peptides might be combined with carriers that increase their immunogenicity, biological activity, and/or stability. In some embodiments, carriers include but are not limited to proteins such as bovine serum albumin (BSA), human serum albumin, immunoglobulins, transferrin, insulin; and/or carbohydrates such as lactose, cellulose, starch. In some embodiments, carriers are proteins such as diphtheria toxoid, tetanus toxoid, influenza virus proteins, and/or herpesvirus proteins. In some embodiments, vaccine compositions comprise any carriers that are safe and acceptable for patients.

In some embodiments, vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, poliovirus vaccines described herein may be administered orally, intramuscularly, subcutaneously or intradermally, similarly to the administration of other inactivated vaccines and VLP vaccines known in the art. Poliovirus vaccine may be utilized in various settings depending on the prevalence of the infection or the degree or level of unmet medical need. In some embodiments, the subject in need thereof is one who is at risk of being infected with poliovirus.

Accordingly, in some embodiments, more than one dose of vaccine is administered to the subject in need thereof. In some embodiments, the more than one dose of vaccine is administered to the subject in a period of time that is less than 2 years. In some embodiments, the more than one dose of vaccine is 2 doses. In some embodiments, the more than one dose of vaccine is 3 doses. In some embodiments, the more than one dose of vaccine is 4 doses or more.

In some aspects, a method of inducing in a subject an immune response against poliovirus comprises administering to the subject a vaccine comprising VLPs in an amount effective to induce an immune response against poliovirus. In some embodiments, the VLPs to be administered to the subject comprise stabilizing mutations that confer a higher degree of thermostability of the N-form of the VLPs.

Formation of Poliovirus Capsid

Mature poliovirions sediment at 150S, contain one copy of the (+) sense, single-strand genomic RNA and have an icosahedral capsid that is made up of 60 copies of each capsid protein (VP1, VP2, VP3 and VP4). In contrast, poliovirus empty capsids sediment at 74S, do not contain any viral RNA and are composed of 60 copies of VP0, VP1 and VP3. As part of the RNA encapsidation and virus maturation process, VP0 undergoes autocatalytic cleavage to form capsid proteins VP2 and VP4, which are present in mature virus particles.

Figure 1A:
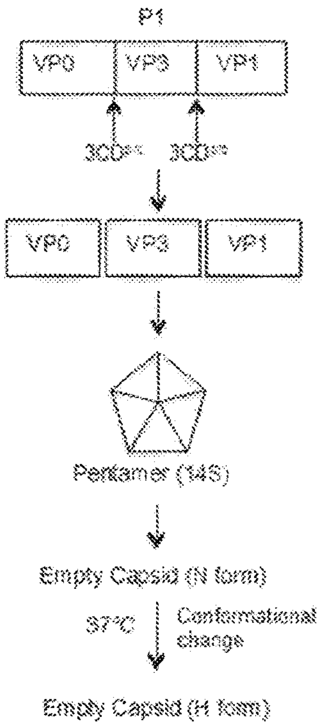
FIG. 1A and FIG. 1B depict formation of poliovirus VLPs in cell-free reactions.

Intermediate structures in the capsid assembly pathway include the 5S protomer and the 14S pentamer. Proteolytic processing of P1, the capsid precursor protein, results in the formation of the 5S protomers, which are then used to form the 14S pentamers and empty capsids. See FIG. 1A. The minimum requirement for empty capsid formation is the expression of the capsid precursor protein, P1, and the viral protease, $3CD^{pro}$. Efficient capsid assembly is only observed when the capsid proteins are first expressed as part of the P1 precursor protein and then processed by $3CD^{pro}$. Therefore, the expression of P1 and $3CD^{pro}$ is the minimum requirement for the formation of recombinant VLPs. Herein, "3CD" and "$3CD^{pro}$" are used interchangeably. Herein, "2A" and "$2A^{pro}$" are used interchangeably. It is to be understood that VLPs mentioned herein refer to recombinant VLPs.

Accordingly, contemplated herein are also nucleic acids encoding PV P1 protein. In some embodiments, a nucleic acid as contemplated herein encodes both PV P1 protein as well as $3CD^{pro}$. In some embodiments, a nucleic acid encodes PV P1, $2A^{pro}$ and $3CD^{pro}$. In some embodiments, a nucleic acid encoding a PV P1, $2A^{pro}$ and/or $3CD^{pro}$ is RNA. Nucleic acids encoding PV P1 as provided herein may encode any one of the PV capsid proteins contemplated herein that result in any one of the PV VLPs that comprise any one or more stabilizing mutations as provided herein. Any one of the nucleic acids encoding any one of the PV P1 protein as disclosed herein can be used in either a cell-free reaction system (e.g., a mammalian cell-free expression system), or introduced into a host cell for protein production (e.g., in mammalian cells, fungus, bacteria, insect cells or plant cells). Nucleic acids encoding any one of the PV P1 proteins disclosed herein may be comprised in vector constructs, e.g., a plasmid or a viral vector (baculovirus vector), which may comprise control elements that may be operably linked to a nucleic acid encoding a PV P1 protein. In some embodiments, a control element is a nucleic acid sequence that affects the expression of the nucleic acid to which it is operably linked. Examples of control elements are promoters, insulators, silencers, response elements, introns, enhancers, initiation sites, termination signals, and poly(A) tails.

Provided herein are also methods of producing PV VLPs comprising any one of the stabilizing mutations described herein. In some embodiments, a method of producing PV VLPs is used to produce N-form PV VLPs. In some embodiments, PV VLPs are produced in cell-free reactions. In some embodiments, PV VLPs are synthesized in cell-free reactions using a capsid expressing nucleic acid, which encodes PV P1, $2A^{pro}$ and $3CD^{pro}$. In some embodiments, PV P1, $2A^{pro}$ and $3CD^{pro}$ are encoded by separate nucleic acids e.g., on separate vectors. For example, three different vectors comprising nucleic acids can encode P1, $2A^{pro}$ and $3CD^{pro}$, respectively. In some embodiments, two of the three proteins of P1, $2A^{pro}$ and $3CD^{pro}$ are encoded by nucleic acids on the same vector while the third is encoded by a nucleic acid on a separate second vector. In some embodiments, translation of proteins is significantly higher (e.g., by 1.1-10 fold, 1.1-2 fold, 1.5-2 fold, 1.5-4 fold, 2-5 fold, 3-6 fold, 5-10 fold or 2-10 fold or more) in the presence of $2A^{pro}$ compared to where P1 and $3CD^{pro}$ are expressed without expression of $2A^{pro}$. In some embodiments, $2A^{pro}$ may stabilize the RNA, or stimulate translation, or both stabilize the RNA and stimulate translation.

In some embodiments, cell-free reactions comprise extract from cells. In some embodiments, HeLa cell extracts are used in cell-free reactions and are referred to as "HeLa cell-free reactions." Capsid expressing nucleic acids, e.g., one that expresses P1, $2A^{pro}$ and $3CD^{pro}$, only expresses the P1 capsid precursor and viral proteases and no other viral replication proteins (e.g., 2B, 2C and 3AB) and therefore cannot replicate. As a result, no infectious material can be formed in cell-free reactions as described herein that produce the PV VLPs using this capsid-expressing RNA. Producing VLPs without the worry of producing infectious PV is of great importance when the VLPs are made to be used as vaccines.

When nucleic acids encoding P1, $2A^{pro}$ and $3CD^{pro}$ proteins are translated in a cell-free reaction, VP0, VP1, VP3, $2A^{pro}$ and $3CD^{pro}$ are produced. In some embodiments, when nucleic acids encoding P1, $2A^{pro}$ and $3CD^{pro}$ proteins are translated in the presence of a labeled methionine, e.g., $[^{35}S]$methionine, labeled proteins VP0, VP1, VP3, $2A^{pro}$ and $3CD^{pro}$ are expressed. Labels (e.g., radioactive labels or fluorescent labels) can be useful in detection of capsid proteins and/or the capsids themselves. In some embodiments, such labeling can be used to monitor expression and production, e.g., during various purification steps.

Cell-free reactions can be run at various conditions. For example, VLPs can be synthesized in a reaction run (e.g., for 6 h) at 30° C. In some embodiments, cell-free reactions to produce any one of the PV VLPs as disclosed herein are run at a temperature below 34° C. (e.g., 33, 32, 31, 30, 29 or less than 29° C.). In some embodiments, cell-free reactions to produce any one of the PV VLPs as disclosed herein are run at a temperature between 30-34° C. (e.g., 30-33, 30-39.9° C.). In some embodiments, cell-free reactions to produce any one of the PV VLPs as disclosed herein are run at a temperature at around 30° C. (+/−1-2° C.).

Several publications explain and demonstrate the use of cell-free PV producing reactions, e.g., Barton et al., Methods Enzymol., 1996, 275:35; Tang et al., RNA, 1997, 3: 624; Molla et al., Science, 1991, 254: 1647; Duggal et al., PNAS, 1997, 94: 13786; and Franco et al., J. Virol., 2005, 6358, which are incorporated herein in their entirely by reference.

Accordingly, in some embodiments, VLPs for use in a vaccine can be prepared by isolating and/or purifying PV capsid proteins (e.g., P1 proteins) and/or VLPs from a cell-free production systems or a cell based production systems that express one or more nucleic acids described herein. In some embodiments, VLPs can be assembled from isolated or purified capsid proteins. Methods of isolating and/or purifying PV capsid proteins and/or VLPs and/or assembling PV VLPs are known in the art and also described in this application.

The sequences provided in this application are examples of sequences for PV1 Mahoney strain (SEQ ID NO. 1-9). Sequences for PV1 Sabin strain can be found in UniProt database. Sequences for representatives of PV2 AND PV3 strains can also be found UniProt database.

In some embodiments, VLPs produced in the mammalian (e.g., human) cell-free systems serve as standards for VLPs that are produced using other protein expression systems (e.g., insect cells, bacterial cells, plant cells, and/or yeast cells).

In addition to being useful in vaccine production, VLPs made in cell-free reactions as described herein are useful for other applications such developing assays to measure the development of PV neutralizing antibodies in vaccinated individuals, e.g., when the use of infectious poliovirus is no longer allowed in lab-based assays. In addition, stable N-form VLPs are useful in isolating and identifying cellular proteins that interact with and bind to virus capsid (e.g., receptor proteins on the cell surface).

In some embodiments, sufficient quantities of the VLPs are directly produced in the scaled-up cell-free reactions.

Amino acid sequence of PV1 VP0

(SEQ ID NO: 1)

GAQVSSQKVGAHENSNRAYGGSTINYTTINYYRDSASNAASKQDFSQDPSKFTEPIKDVLIKTAPMLNSPNIEACGYSDRVLQ

LTLGNSTITTQEAANSVVAYGRWPEYLRDSEANPVDQPTEPDVAACRFYTLDTVSWTKESRGWWWKLPDALRDMGLFGQNMYY

HYLGRSGYTVHVQCNASKFHQGALGVFAVPEMCLAGDSNTTTMHTSYQNANPGEKGGTFTGTFTPDNNQTSPARRFCPVDYLL

GNGTLLGNAFVFPHQIINLRTNNCATLVLPYVNSLSIDSMVKHNNWGIAILPLAPLNFASESSPEIPITLTIAPMCCEFNGLR

NITLPRLQ

Amino acid sequence of PV1 VP4

(SEQ ID NO: 2)

GAQVSSQKVGAHENSNRAYGGSTINYTTINYYRDSASNAASKQDFSQDPSKFTEPIKDVLIKTAPMLN

Amino acid sequence of PV1 VP2

(SEQ ID NO: 3)

SPNIEACGYSDRVLQLTLGNSTITTQEAANSVVAYGRWPEYLRDSEANPVDQPTEPDVAACRFYTLDTVSWTKESRGWWWKLP

DALRDMGLFGQNMYYHYLGRSGYTVHVQCNASKFHQGALGVFAVPEMCLAGDSNTTTMHTSYQNANPGEKGGTFTGTFTPDNN

QTSPARRFCPVDYLLGNGTLLGNAFVFPHQIINLRTNNCATLVLPYVNSLSIDSMVKHNNWGIAILPLAPLNFASESSPEIPI

TLTIAPMCCEFNGLRNITLPRLQ

Amino acid sequence of PV1 VP3

(SEQ ID NO: 4)

GLPVMNTPGSNQYLTADNFQSPCALPEFDVTPPIDIPGEVKNMMELAEIDTMIPFDLSATKKNTMEMYRVRLSDKPHTDDPIL

CLSLSPASDPRLSHTMLGEILNYYTHWAGSLKFTFLFCGFMMATGKLLVSYAPPGADPPKKRKEAMLGTHVIWDIGLQSSCTM

VVPWISNTTYRQTIDDSFTEGGYISVFYQTRIVVPLSTPREMDILGFVSACNDFSVRLLRDTTHIEQKALAQ

Amino acid sequence of PV1 VP1

(SEQ ID NO: 5)

GLGQMLESMIDNTVRETVGAATSRDALPNTEASGPTHSKEIPALTAVETGATNPLVPSDTVQTRHVVQHRSRSESSIESFFAR

GACVTIMTVDNPASTTNKDKLFAVWKITYKDTVQLRRKLEFFTYSRFDMELTFVVTANFTETNNGHALNQVYQIMYVPPGAPV

PEKWDDYTWQTSSNPSIFYTYGTAPARISVPYVGISNAYSHFYDGFSKVPLKDQSAALGDSLYGAASLNDFGILAVRVVNDHN

PTKVTSKIRVYLKPKHIRVWCPRPPRAVAYYGPGVDYKDGTLTPLSTKDLTTY

Amino acid sequence of PV1 3CD (SEQ ID NO: 6)

GPGFDYAVAMAKRNIVTATTSKGEFTMLGVHDNVAILPTHASPGESIVIDGKEVEILDAKALEDQAGTNLEITIITLKRNEKF

RDIRPHIPTQITETNDGVLIVNTSKYPNMYVPVGAVTEQGYLNLGGRQTARTLMYNFPTRAGQCGGVITCTGKVIGMHVGGNG

SHGFAAALKRSYFTQSQGEIQWMRPSKEVGYPIINAPSKTKLEPSAFHYVFEGVKEPAVLTKNDPRLKTDFEEAIFSKYVGNK

ITEVDEYMKEAVDHYAGQLMSLDINTEQMCLEDAMYGTDGLEALDLSTSAGYPYVAMGKKKRDILNKQTRDTKEMQKLLDTYG

INLPLVTYVKDELRSKTKVEQGKSRLIEASSLNDSVAMRMAFGNLYAAFHKNPGVITGSAVGCDPDLFWSKIPVLMEEKLFAF

DYTGYDASLSPAWFEALKMVLEKIGFGDRVDYIDYLNHSHHLYKNKTYCVKGGMPSGCSGTSIFNSMINNLIIRTLLLKTYKG

IDLDHLKMIAYGDDVIASYPHEVDASLLAQSGKDYGLTMTPADKSATFETVTWENVTFLKRFFRADEKYPFLIHPVMPMKEIH

ESIRWTKDPRNTQDHVRSLCLLAWHNGEEEYNKFLAKIRSVPIGRALLLPEYSTLYRRWLDSF

Amino acid sequence of PV1 3C (SEQ ID NO: 7)

GPGFDYAVAMAKRNIVTATTSKGEFTMLGVHDNVAILPTHASPGESIVIDGKEVEILDAKALEDQAGTNLEITIITLKRNEKF

RDIRPHIPTQITETNDGVLIVNTSKYPNMYVPVGAVTEQGYLNLGGRQTARTLMYNFPTRAGQCGGVITCTGKVIGMHVGGNG

SHGFAAALKRSYFTQS

Amino acid sequence of PV1 P1

(SEQ ID NO: 8)

GAQVSSQKVGAHENSNRAYGGSTINYTTINYYRDSASNAASKQDFSQDPSKFTEPIKDVLIKTAPMLNSPNIEACGYSDRVLQ

LTLGNSTITTQEAANSVVAYGRWPEYLRDSEANPVDQPTEPDVAACRFYTLDTVSWTKESRGWWWKLPDALRDMGLFGQNMYY

HYLGRSGYTVHVQCNASKFHQGALGVFAVPEMCLAGDSNTTTMHTSYQNANPGEKGGTFTGTFTPDNNQTSPARRFCPVDYLL

-continued

GNGTLLGNAFVFPHQIINLRTNNCATLVLPYVNSLSIDSMVKHNNWGIAILPLAPLNFASESSPEIPITLTIAPMCCEFNGLR

NITLPRLQGLPVMNTPGSNQYLTADNFQSPCALPEFDVTPPIDIPGEVKNMMELAEIDTMIPFDLSATKKNTMEMYRVRLSDK

PHTDDPILCLSLSPASDPRLSHTMLGEILNYYTHWAGSLKFTFLFCGFMMATGKLLVSYAPPGADPPKKRKEAMLGTHVIWDI

GLQSSCTMVVPWISNTTYRQTIDDSFTEGGYISVFYQTRIVVPLSTPREMDILGFVSACNDFSVRLLRDTTHIEQKALAQGLG

QMLESMIDNTVRETVGAATSRDALPNTEASGPTHSKEIPALTAVETGATNPLVPSDTVQTRHVVQHRSRSESSIESFFARGAC

VTIMTVDNPASTTNKDKLFAVWKITYKDTVQLRRKLEFFTYSRFDMELTFVVTANFTETNNGHALNQVYQIMYVPPGAPVPEK

WDDYTWQTSSNPSIFYTYGTAPARISVPYVGISNAYSHFYDGFSKVPLKDQSAALGDSLYGAASLNDFGILAVRVVNDHNPTK

VTSKIRVYLKPKHIRVWCPRPPRAVAYYGPGVDYKDGTLTPLSTKDLTTY

Amino acid sequence of PV1 2A (SEQ ID NO: 9)

GFGH QNKAVYTAGYKICNYHLATQDDLQNAVNVMWSRDLLVTESRAQGTDSIARCNCNAGVYYCESRRKYYPVSFVGPTFQY

MEANNYYPARYQSHMLIGHGFASPGDCGGILRCHHGVIGIITAGGEGLVAFSDIRDLYAYEEEAMEQ

N-Antigenic Form of VLPs

When empty capsids are initially made in cells they are antigenically identical to mature virus (e.g., N-antigenic form, or N-form) (Icenogle, J. et al., Virology 115:211-215, 1981). See FIG. 1A. This is consistent with structural studies which show that the outer surface of the N-form of the native empty capsid is very similar to that of the mature virus (Basavappa, R et al., Protein Sci. 3:1651-1669, 1994). However, the N-form empty capsid undergoes a conformational change and is converted to the H- (heat-denatured-) form upon exposure to physiological temperatures (Rombaut, B. et al., Virology 157:245-247, 1987; Rombaut, B. et al., Arch. Virol. 106:213-220, 1989). The H-form empty capsid does not have the neutralizing antigenic sites and therefore is incapable of producing neutralizing antibodies. Therefore, in some embodiments, an effective VLP vaccine comprises N-form empty capsids that are sufficiently thermostable so that they don't undergo the conformational change.

Figure 1B:
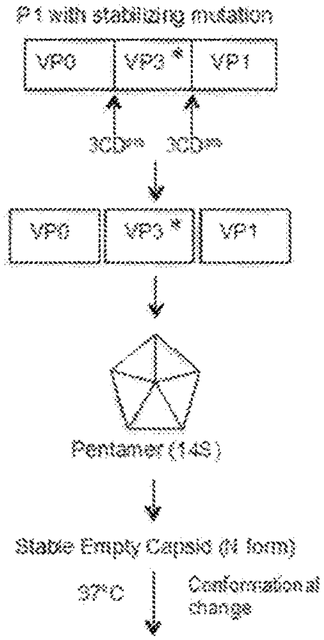

Since the N antigenic form of the empty capsid closely mimics wildtype virus, it can serve as an alternative for producing a non-infectious poliovirus vaccine. The challenge, however, is to engineer recombinant empty capsids, or VLPs, which remain in the N-form under physiological conditions (FIG. 1B). In some embodiments, these recombinant VLPs will be both non-infectious and immunogenic (e.g., produce neutralizing antibodies) without having the shortcomings of the current vaccines. In particular, it will not be necessary to use wildtype seed virus (or even a live attenuated strain) to produce an inactivated vaccine. This will dramatically increase the safety and reduce the cost of vaccine production. The availability of this type of vaccine will be extremely useful both in the pre- and post-eradication world and can accelerate achieving a polio-free world.

Production, Purification and Storage of VLPs

Herein, the terms "synthesized", "produced", and "generated" are used synonymously. Methods of forming recombinant empty capsids or VLPs using different expression systems, e.g., mammalian cells, yeast, bacteria, insect cells and plant cells, are known, see e.g., Brautigam, S., et al., Virology 192:512-524, 1993; Chung, et al., Vaccine 28:6951-6957, 2010; Ku, Z et al., Vaccine 32:4296-4303, 2014; Li, H. Vaccine 31:3281-3287, 2013; Liu, Q et al., J. Virol. Methods 187:127-131, 2013; Porta, C. et al., PLoS. Pathog. 9:e1003255, 2013; Rombaut, B. Jore, J., J. Gen. Virol. 78 (Pt 8):1829-1832, 1997, which are incorporated herein by reference in their entirety. Methods for large-scale production of VLPs for various viruses are also known in the art, and can be adapted for production of PV VLPs as disclosed here. For example, Vincente et al. (J Invertebr Pathol. 2011; 107 Suppl:S42-8) discusses choices and trends of large-scale production and purification of VLP-based vaccines generated through the baculovirus expression vector system using insect cells, and Xiao et al. (BMC Biotechnol. 2016; 16(1):56) discusses large-scale production of foot-and-mouth disease virus VLP vaccine in *E. Coli*, Thompson et al. (BMC Biotechnol. 2015; 15:31) assesses influenza VLP production in Sf9 and HEK293 expression systems, the disclosures of each of which are incorporated by reference in their entirety.

In some embodiments, any one of the VLPs described herein are synthesized in cell-free extracts or reactions. In some embodiments, VLPs are synthesized in HeLa cell-free extracts or reactions. In some embodiments, PV VLPs are synthesized in HeLa cell-free reactions using a capsid expressing RNA, which encodes PV P1 precursor protein and $3CD^{pro}$. In some embodiments, PV P1, and $3CD^{pro}$ encoding RNA are used in cell-free reactions for synthesizing VLPs. In some embodiments, PV P1, $3CD^{pro}$ and $2A^{pro}$ encoding RNA are used in cell-free reactions for synthesizing VLPs. The viral protease, 2A, is known to enhance translation. In some embodiments, a single expression RNA to produce P1, and the viral proteases, $2A^{pro}$ and $3CD^{pro}$ is used to synthesize VLPs. In some embodiments, more than one expression RNAs to produce P1, and the viral proteases, $2A^{pro}$ and $3CD^{pro}$ are used to synthesize VLPs. In some embodiments, a single expression RNA to produce P1, and the viral proteases, $2A^{pro}$, 3CP" and $3CD^{pro}$ is used to synthesize VLPs. In some embodiments, more than one expression RNAs are used to produce P1, and the viral proteases, $2A^{pro}$, 3CP" and $3CD^{pro}$ are used to synthesize VLPs.

In some embodiments, PV VLPs are synthesized using cell-free reactions carried out at 34° C. In some embodiments, PV VLPs are synthesized using cell-free reactions carried out at 30° C. In some embodiments, PV VLPs are synthesized using cell-free reactions carried out at a temperature ranging from 30° C. to 34° C. In some embodiments, PV VLPs are synthesized using cell-free reactions carried out at around 30° C. (+/−1-2° C.). In some embodiments, PV VLPs are synthesized using cell-free reactions carried out at a temperature ranging from 25° C. to 34° C. In some embodiments, PV VLPs are synthesized using cell-free reactions carried out at a temperature ranging from 20° C. to 37° C. In some embodiments, PV VLPs are synthesized using cell-free reactions carried out at a temperature ranging from 15° C. to 40° C. In some embodiments, PV VLPs are synthesized using cell-free reactions carried out at a temperature ranging from 15° C. to 45° C., or higher. In some embodiments, the PV VLPs are synthesized using cell-free reactions carried out for 4 h. In some embodiments, the PV VLPs are synthesized using cell-free reactions carried out for 6 h. In some embodiments, the PV VLPs are synthesized using cell-free reactions carried out for 17 h. In some embodiments, the PV VLPs are synthesized using cell-free reactions carried out for a time period ranging from 0.5 h to 20 h. In some embodiments, the PV VLPs are synthesized using cell-free reactions carried out for a time period ranging from 0.01 h to 40 h. In some embodiments, the PV VLPs are synthesized using cell-free reactions carried out for a time period ranging from 0.01 h to 100 h. In some embodiments, the PV VLPs are synthesized using cell-free reactions carried out for a time period ranging from 2 h to 1000 h.

In some embodiments, PV VLPs are synthesized using other cell-free reactions or in cell-based production systems.

In some embodiments, the N-antigenic units (NU) of VLPs synthesized in cell-free reactions range from 6±1 NU/μl to 10±3 NU/μl for the wildtype and mutant VLPs, respectively. In such embodiments, a 100 μl reaction yields 600 NU for wildtype VLPs and 1000 NU for mutant VLPs. In some embodiments, the wildtype or N-antigenic units (NU) of VLPs synthesized in cell-free reactions range from 1 NU/μl to 10 NU/μl. In some embodiments, the N-antigenic units (NU) of VLPs synthesized in cell-free reactions range from 0.1 NU/μl to 100 NU/μl.

In some embodiments, wildtype and mutant VLPs are purified by sucrose gradient centrifugation. In some embodiments, a sucrose gradient of 15-30% is used for purification of VLPs. In some embodiments, the sucrose gradient centrifugation is performed at 4° C. In some embodiments, the sucrose gradient centrifugation is performed at temperature in the range of 4-40° C. In some embodiments, only the capsid proteins, VP0, VP1 and VP3 comprise the peak fractions in sucrose gradient centrifugation. In some embodiments, additional purification of the VLPs for the purpose of antibody production is carried out. In some embodiments, HeLa cell-free VLP synthesis reactions are scaled up. Scaling up of reactions accommodate for losses of NU in additional purification steps. In some embodiments, HeLa cell-free VLP synthesis reactions are scaled up by 10 fold. In some embodiments, HeLa cell-free VLP synthesis reactions are scaled up by 2-20 fold. In some embodiments, the HeLa cell-free VLP synthesis reactions are scaled up by 20-100 fold. In some embodiments, 10-25% of the starting material is recovered after multi-step purification. In some embodiments, 5-40% of the starting material is recovered after multi-step purification. In some embodiments, 2-90% of the starting material is recovered after multi-step purification.

Methods of purifying AAV VLPs for analysis by electron microscopy are known in the art and can also be adapted for purifying PV VLPs (Lane, M. et al., Acta Crystallogr Sect F Struct Biol Cryst Commun. 61:558-561, 2005), and are incorporated herein by reference in their entirety. In some embodiments, the production of VLPs is scaled up to accommodate characterization by one or more of the following techniques: TEM, cryo-TEM, differential scanning fluorimetry (DSF), and differential scanning calorimetry (DSC).

In some embodiments, PV VLPs are isolated from infected HeLa cells. Methods of purifying PV VLPs from HeLa cells are known in the art (Basavappa, R. et al., Protein Sci. 3:1651-1669, 1994), and are herein incorporated by reference in their entirety. In some embodiments, purified empty capsids are crystallized and used for structural analysis.

In some embodiments, formed VLPs in the N-antigenic form are maintained by incubation of cell-free reactions at 30° C. In some embodiments, formed VLPs in the N-antigenic form are maintained by incubation of cell-free reactions at 4° C. In some embodiments, formed VLPs in the N-antigenic form are maintained by incubation of cell-free reactions at a temperature in the range of 4° C. to 30° C. In some embodiments, formed VLPs in the N-antigenic form are maintained by running the sucrose gradients at 4° C. In some embodiments, formed VLPs in the N-antigenic form are maintained by storage of purified VLPs at 4° C. In some embodiments, formed VLPs in the N-antigenic form are maintained by storage of purified VLPs at −80° C. In some embodiments, formed VLPs in the N-antigenic form are maintained by storage of purified VLPs at a temperature in the range of 4° C. to −80° C. In some embodiments, formed VLPs in the N-antigenic form are maintained by storage of purified VLPs in liquid nitrogen storage.

In some embodiments, the concentration of the VLPs in the disclosed compositions is $1\times10^{8}$ particles/W. In some embodiments, the concentration of the VLPs in the disclosed compositions is in the range of $1\times10^{8}$ particles/W to $1\times10^{12}$ particles/W. In some embodiments, the concentration of the VLPs in the disclosed compositions is in the range of $1\times10^{5}$ particles/μl to $1\times10^{15}$ particles/W. In some embodiments, the concentration of the VLPs in the disclosed compositions is in the range of 1 particle/μl to $1\times10^{20}$ particles/W.

In Vitro Characterization of the PV VLPs

In some embodiments, characterization is done to assess proper capsid assembly. In some embodiments, characterization is done to assess thermostability. In some embodiments, characterization is done to assess location of antibody neutralizing epitopes. In some embodiments, characterization is done to assess conservation of viral protein secondary structure. Methods of making these assessments are known to those skilled in the art.

In vitro characterization of the disclosed PV VLPs can be performed using various techniques. In some embodiments, to determine if VLPs are assembled the P1 and protease expression RNA is translated in reactions containing [$^{35}$S] methionine. The labeled viral protein products synthesized in these reactions are then fractionated by centrifugation on a 15-30% sucrose gradient, and the 74S peak fractions containing the labeled VLPs are subject to the ELISA described below to quantitate the antigenic form of the VLPs.

In some embodiments, the disclosed VLPs are imaged using transmission electron microscopy (TEM) to observe size and morphology of the VLPs. In some embodiments, the disclosed VLPs are imaged using cryo-TEM. In some embodiments, cryo-TEM is used to image VLPs that are complexed with PV receptor or an N-form specific antibody, to determine the antigenic sites on the VLPs. In some embodiments, process of assessing the antigenic sites on the VLPs involves one or more of the following steps: complexing purified VLPs with the Novus 14D2(7C5) monoclonal antibody, or CD155, a known poliovirus receptor; freezing the VLP-antibody complex onto holey carbon grids; and manual or automated-manual image collection on TEM. In some embodiments, the three-dimensional VLP-antibody complex is reconstructed, confirming the antibody-binding residues on the capsid surface and, therefore, verifying the N-antigenic nature of the capsids.

In some embodiments, additional information such as predicted binding energy is obtained by using a combination of publicly available and licensed software such as the PDBePISA suite, Coot, and UCSF Chimera. In some embodiments, the wildtype capsid is compared to the VP3 (178Q.L) mutant to elucidate the actual change in residue interactions at the VP3 178 position.

In some embodiments, thermostability of VLPs is assessed using biophysical assays such as differential scanning fluorimetry (DSF) and differential scanning calorimetry (DSC). In DSF, the exposure of internal hydrophobic regions of viral proteins is measured with a fluorescent dye that binds to these locations upon an unfolding event. With DSC, the thermal transitions can be ascertained precisely, as endothermic events are readily denoted by changes in enthalpy as a function of heat-flux.

In some embodiments, the overall preservation of secondary structure of the poliovirus capsid is measured using circular dichroism.

ELISA for the Detection of N-Form PV VLPs

When empty capsids are made in cells, they are in the N-antigenic form and are identical to mature virus. An ELISA was established to determine the antigenic form of the VLPs produced both from cells or in cell-free reactions. In some embodiments, this ELISA is used to confirm that the VLPs are in N-antigenic form. In some embodiments, the ELISA is used to quantitate the N-form or N-antigenic titers of the disclosed VLPs. A PV1 antibody, 14D2 (7C5) (available from Novus Biologicals, Littleton, Colo.) has been previously characterized by the Centers of Disease Control (CDC) for its specificity in detecting PV1 capsids in the N-antigenic form. Their results showed that the Novus 14D2(7C5) antibody is very specific for the N-antigenic form of the capsid and was the best antibody tested for distinguishing between the N- and H-antigenic forms of the virus capsid. In some embodiments, standard curves are produced using IPV, which can be purchased from Sanofi Pasteur. In some embodiments, a linear curve established by the recognition of the N-form type 1 poliovirus in the IPV in the ELISA by 14D2(7C5) monoclonal antibody is used. In some embodiments, N-antigenic units/μl for assembled VLPs and for IPV are calculated using the NIBSC International Standard for IPV (NIBSC code: 12/104), which is used in the preparation of commercial IPV. In some embodiments, reported N-antigenic titers are based on this WHO International Reference PV1 IPV Standard.

In some embodiments, [$^{35}$S] methionine labeled VLPs are produced and fractionated on a 15-30% sucrose gradient and the resultant fractions are all subjected to the described ELISA to confirm that the N-antigenic titer that was obtained for the unfractionated VLP composition derives from assembled VLPs and not from individual capsid proteins.

In Vivo Characterization and Microneutralization Analysis of Antibodies Produced from VLPs The US Centers for Disease Control and Prevention (CDC, Atlanta, Ga., USA) provide an in vivo characterization and microneutralization analysis of antibodies produced from the VLPs provided to them as antigenic material. Wistar rats are used for antibody production. 8-10 rats are immunized with the PV1 wildtype and PV1 VP3(178Q.L) VLPs. An antigenic load of 8 N-antigenic units (NU), also referred to as D-antigenic units, per animal is sufficient for a robust immune response and since the response in the Wistar rat is robust, generally one immunization is sufficient. A "robust immune response" is one which results in the production of sufficient amount of neutralizing antibodies to provide immunity against PV infection. In some embodiments, IPV is used as a positive control. In some embodiments, 100 NU of purified VLPs are used in such an immunization protocol. In some embodiments, 50-150 NU of purified VLPs are used in such an immunization protocol. In some embodiments, 80-120 NU of purified VLPs are used in such an immunization protocol. The N-antigen units for wildtype or mutant VLPs as well as the IPV is standardized using the WHO-NIBSC International Standard for IPV (NIBSC code: 12/104).

The neutralization titers of the antisera isolated from immunized rats are determined using the WHO microneutralization test. Methods of this WHO microneutralization test is known (Albrecht, P. et al., J. Biol Stand. 11:91-97, 1983), and is herein incorporated by reference in their entirety. A VLP with a high thermostability of its N-antigenic form will produce high neutralization titers, which a VLP that loses N-antigenicity rapidly in time-course experiments at 37° C. will produce a low neutralizing antibody titer.

In some embodiments, if the stable N-form mutant VLPs from two PV serotypes produce high-titer neutralizing antibodies, then a bivalent mix of stable VLPs can be tested in animals to see if neutralizing antibodies to both serotypes can be produced in vivo. This would provide the experimental basis for the development of a non-infectious, bivalent poliovirus VLP vaccine. In some embodiments, the bivalent poliovirus VLP vaccine comprises PV1 and PV2 VLPs. In some embodiments, the bivalent poliovirus VLP vaccine comprises PV1 and PV3 VLPs. In some embodiments, the bivalent poliovirus VLP vaccine comprises PV2 and PV3 VLPs. In some embodiments, a poliovirus vaccine as disclosed herein can comprise VLPs from PV1, PV2 and PV3.

In some embodiments, if the stable N-form mutant VLPs from all three poliovirus serotypes produce high-titer neutralizing antibodies, then a trivalent mix of stable VLPs can be tested in animals to determine whether neutralizing antibodies to all three serotypes can be produced in vivo. This provides a basis for the development of a non-infectious, trivalent poliovirus VLP vaccine.

It is to be understood that the approach of designing stabilizing mutations to develop VLPs for use as vaccines can be applied to other viruses. In some embodiments, the other viruses are enteroviruses. In some embodiments, the enteroviruses are a human enteroviruses.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: PV1 VLPs

This example illustrates that thermostable PV1 VLPs in the N-form can be constructed by the rational design of capsid mutations and then produced in cell-free reactions. Characterization of the thermostable PV1 VLPs is also provided.

The objective is to produce and purify an amount of PV1 wildtype and mutant VLPs in cell-free reactions that is sufficient to allow the determination of the immunogenicity of the wildtype and mutant VLPs, which would involve comparing the PV neutralizing antibody titers to the values obtained using IPV. Once purified, VLPs can then be characterized for sedimentation on sucrose gradients, N-antigenic titer, thermostability and visualized by transmission electron microscopy (TEM). For immunization studies, the US Centers for Disease Control and Prevention (CDC, Atlanta, Ga., USA) provide an in vivo characterization and microneutralization analysis of antibodies that are produced from the VLPs provided as antigenic material.

Design of Stabilizing Mutations that Confer a Higher Degree of Thermostability of the N-Form of the VLPs When exposed to physiological temperatures, N-form PV1 VLPs are known to undergo a conformational change and are converted to the H (heat-denatured) antigenic form. The H-form empty capsids do not contain neutralizing antigenic sites and, therefore, cannot produce neutralizing antibodies. Based on an in silico analysis, capsid mutations that are predicted to increase the stability of the N-form mutant VLPs were designed (Table 1). VP3(167V.D) mutation is predicted to create a hydrogen-bond interaction with VP3(167D) and VP1(60T) and significantly increase capsid stability. VP1(231A.V) is a previously characterized soluble receptor-binding mutation, as is the VP3(178Q.L) mutation (Colston, E. and Racaniello, V, EMBO J. 13:5855-5862, 1994). In this case, Van der Waals interactions increase between VP1(231V) and both VP1(228L) and VP2(141M). It is possible that introducing different individual mutations or combinations of mutations will result in stabilizing the capsid even further or allow the capsid to assemble into a more immunogenic structure overall.

TABLE 1

PV N-form VLP stabilizing mutations:

| Category | Capsid Mutation | Binding Partner(s) | Binding Interaction | Δ[−ΔG] (Kcal/ml)[a] |
|---|---|---|---|---|
| 1. New in silico derived stablilizing mutations | VP3(202L.E) | VP3(202S) VP2(242E) | H-bond | 84 |
| | VP3(167V.D) | VP1(60T) | H-bond | 144 |
| | VP3(4V.C) | VP3(4VC) | Disulfide | 312 |
| | VP1(147N.C) | VP1(147N.C) | Disulfide | 132 |
| 2. Sabin tss mutation | VP2(201R.K) | VP3(126A) | H-bond | 90 |
| 3. Receptor binding mutation | VP1(231A.V) | VP1(228L) VP2(141M) | van der Waals | 90 |
| 4. tss/receptor binding mutation | VP3(178Q.L) | VP1(201I) VP3(180I) | van der Waals | 78 |

[a]Δ[−ΔG] is the difference in Gibbs free energy between mutant capsid and wildtype. This represents the additional energy required to destabilize the mutant capsid relative to wildtype.
tss: temperature sensitive suppressor.

Purification of VLPs from HeLa Cell Free Reactions

N-form PV1 VP3(178Q.L) VLPs were produced in HeLa cell-free reactions. Wildtype and mutant PV1 VLPs were synthesized in HeLa cell-free reactions using a capsid expressing RNA, which encodes PV1 P1, $2A^{pro}$ and $3CD^{pro}$, herein also referred to as PV1-P1-2A-3CD. This capsid expressing RNA, P1-2A-3CD, only expresses the P1 capsid precursor and the viral proteases and no other viral replication proteins (e.g., 2B, 2C and 3AB) and cannot replicate. Therefore, no infectious material can be formed in the cell-free reactions that produce the PV VLPs using this capsid-expressing RNA.

When P1-2A-3CD RNA is translated in HeLa cell-free reactions in the presence of [$^{35}$S]methionine, the predicted labeled proteins, VP0, VP1, VP3, $2A^{pro}$ and $3CD^{pro}$ are efficiently expressed (FIG. 2). Translation of the VP3 (178Q.L) and VP3(202L.E) mutant RNAs resulted in the synthesis and proteolytic processing of labeled PV1 proteins at levels equivalent to those observed in reactions containing the wildtype expression RNA. Viral protein 3D', which is a known $2A^{pro}$ cleavage product of 3CD, was also found to be present as expected. These results indicated that the two VP3 mutations had no effect on the synthesis or proteolytic processing of the viral capsid proteins.

These results demonstrate the feasibility of using a single expression RNA to efficiently produce P1, and the viral proteases, $2A^{pro}$, 3CP" and $3CD^{pro}$. VLPs were synthesized in a reaction run for 6 h at 30° C. Translation was significantly higher in the presence of $2A^{pro}$ than were observed in other experiments where P1 and $3CD^{pro}$ were expressed from separate RNAs.

Characterization of VLPs Using Sucrose Gradient Centrifugation

To determine if VLPs were assembled at 30° C., P1-2A-3CD RNA was translated for 6 h at 30° C. in reactions containing [$^{35}$S]methionine. The labeled viral protein products synthesized in this reaction were then fractionated by centrifugation on a 15-30% sucrose gradient run at 4° C. The resultant fractions, including the 74S peak fraction containing the labeled VLPs, were characterized using the ELISA using the 14D2(7C5) N-specific antibody described herein. The results show that the N-antigen levels in the 74S peak fractions correspond directly with the amount of $^{35}$S-labeled VLPs that were present in each fraction. Importantly, the response in the ELISA was dose-specific with the peak fraction giving the strongest signal. The unassembled capsid proteins (VP0, VP1 and VP3) were recovered in fractions in the upper portion of a 15-30% sucrose gradient. Fractions from this part of the gradient were also analyzed using the ELISA, but they did not produce a signal above background levels.

The peak fractions containing the labeled VLPs were next analyzed by SDS-PAGE. As expected, capsid proteins, VP0, VP1 and VP3 were the only labeled viral proteins present in the peak fraction. This result indicated that the labeled 74S peak fraction consisted of labeled PV1 VLPs. To increase the yield of purified VLPs assembled in the cell free reactions, the yield of labeled VLPs recovered from cell-free reactions run for 6h and 17h were compared. The results from this experiment showed that the yield of VLPs was increased about 1.4 fold in the 17 h reaction.

To determine if mutant VLPs sediment to the same position as wildtype VLPs in a 15-30% sucrose gradient, PV1VP3(178Q.L) VLPs were synthesized in HeLa cell-free reactions at 30° for 17 h in the presence of [$^{35}$S]methionine. The labeled proteins were fractionated on a 15-30% sucrose gradient and the peak fractions were detected by TCA precipitation (FIG. 3A and FIG. 3B). In addition, the N-antigen units in selected peak fractions were determined by ELISA. The results showed that both the wildtype and PV1VP3(178Q.L) VLPs sedimented to the same position (74S) in a 15-30% sucrose gradients run under identical conditions. In addition, the N-antigen units measured in the ELISA co-sedimented with the peak of radioactivity in both wildtype and VP3(178Q.L) VLP gradients. Based on these results, it was concluded that N-antigenic VLPs sedimenting at 74S were assembled in both the wildtype and the VP3 (178Q.L) reactions.

N-Antigenic Titers

The ELISA described herein was used to measure the N-antigenic titer of the wildtype, PV1 VP3(178Q.L) and PV1 VP3(202L.E) VLPs assembled in HeLa cell-free reactions. As described earlier, the ELISA can be used to determine the N-antigenic titer of PV1 VLPs produced in cell-free translation reactions. Cell-free reactions containing wildtype, VP3(178Q.L) or VP3(202L.E) expression RNAs were translated at 30° for 17 h. A portion of each reaction contained [$^{35}$S]methionine to monitor protein synthesis and to ensure that all RNA transcripts translated equally. The cell-free translation reactions were diluted 500-fold for use in the ELISA. The N-antigenic units produced in the reaction containing the PV1 VP3(178Q.L) VLPs was about 1.6 fold higher than in the reaction containing the wildtype PV1 VLPs (Table 2), suggesting that the N-form PV1VP3 (178Q.L) VLPs were either more stable or assembled more efficiently than the wildtype VLPs in the cell free reactions. In marked contrast, the N-antigenic titer of the reaction containing the PV1VP3(202L.E) VLPs was about 3.2 fold lower that the reaction containing the wildtype VLPs (Table 2).

TABLE 2

Titer of N-antigenic PV1 VLPs assembled in HeLa cell-free reactions:

| PV1 VLPs | N-antigenic units/μl |
|---|---|
| Wildtype | 6.15 ± 0.95 |
| VP3(202L.E) | 1.92 ± 1.39 |
| VP3(178Q.L). | 9.76 ± 2.59 |

N-Form PV1 VLPs in Unfractionated HeLa Cell-Free Translation Reactions

PV1 VLPs were synthesized as before using the capsid expressing RNA, P1-2A-3CD. A portion of the reaction was removed and labeled with [$^{35}$S]methionine to monitor protein synthesis. A mock reaction that did not contain any PV1 RNA was used as a negative control. The results of the ELISA showed that the N-antigenic titer was very high in the cell-free reaction containing the PV1 VLPs compared to the mock control. The cell-free reactions had to be diluted >10 fold to get into the linear range of the ELISA. This result shows that PV1 VLPs can be analyzed in the diluted complete reaction, which simplifies the initial analysis of capsid mutations that were designed to stabilize the N-form of PV1 VLPs.

Characterization of VLPs Using Transmission Electron Microscopy (TEM)

The PV1 VP3(178Q.L) VLPs were sedimented on a 15-30% sucrose gradient and the 74S peak of N-antigenic activity was identified by ELISA. The peak fractions were pooled and the PV1 (VP3 178Q.L) VLPs were pelleted by ultracentrifugation. The pellet was resuspended and a portion of the resuspended VLPs was characterized by TEM (FIG. 4). VLPs of the expected size (30 nm) and morphology were observed in electron micrographs at three levels of magnification. The N-form PV1VP3(178Q.L) VLPs appeared to be identical in size and structure to wildtype VLPs previously visualized by TEM.

N-Antigenic Stability and Immunogenicity

Previous studies have shown that wildtype VLPs are unstable at 37° C. and undergo a conformational change from the native N-form to the H-form. Based on an in silico analysis, it was predicted that the VP3(178Q.L) VLPs and the VP3(202L.E) VLPs should have increased stability relative to the wildtype VLPs. Unfortunately, the N-antigenic titer of the VP3 202L.E VLPs was about 3 times lower than wildtype VLPs (Table 2). In contrast, the N-antigenic titer of the VP3(178Q.L) VLPs was significantly higher than the values observed with wildtype VLPs (Table 2). Thus, VP3(178Q.L) VLPs may be a candidate for use in an inactivated vaccine if they are more stable than wildtype VLPs at 37° C. and above. Therefore, the stability of wildtype VLPs and VP3(178Q.L) VLPs in time-course experiments at 37° C. and 39° C. were compared. In these experiments, inactivated poliovirus type 1 (IPV) was used as a control since it has a stable N-form capsid at these temperatures.

A time-course experiment was carried out to determine the thermostability of the N-antigenic form of the wildtype and mutant VLPs at 39° C. (FIG. 5). As expected, the N-antigenic titer of the IPV control was stable (within experimental error) during the 8 h incubation period. Consistent with previous studies, the wildtype VLPs were unstable at 39° C. and the N-antigenic titer decreased to base line levels during the first 2 h of the assay (FIG. 5). In marked contrast, the N-antigenic titer of the VP3(178Q.L) VLPs was stable during the 8 h incubation period and were similar to the results observed with the IPV control. The N-antigenic titer of VP3(202L.E) VLPs was low and remained at this level during the 8 h assay.

To examine the long-term stability of the PV1VP3 (178Q.L) VLPs, 48 h time-course experiments at 37° C. and 39° C. were conducted (FIG. 6). As predicted, the wildtype VLPs were unstable and the N-antigenic titer decreased to background levels by 8 h. The N-antigenic titer of the VP3(178Q.L) VLPs, however, was stable during the entire 48 h incubation period at both 37° C. and 39° C. Remarkably, the VP3(178Q.L) VLPs were equivalent in stability to the IPV control at both temperatures (FIG. 6). Based on these results, this experiment was repeated at 37° C. but extended the incubation period to 5 days (FIG. 7). The wildtype VLPs were unstable and rapidly lost their N-antigenic titer. The N-antigenic titer of the VP3(178Q.L) VLPs was stable during 5-day incubation and was equivalent in stability to the IPV control. This 5-day time-course was repeated at 39° C. with similar results. Therefore, these results demonstrate that the VP3(178Q.L) VLPs are stable in the N-antigenic form for up five days when incubated at 37° C. or 39° C. In addition, the results show that the VP3 (178Q.L) VLPs are equivalent to the stability of inactivated PV1 in IPV.

Because PV1 VP3(178Q.L) VLPs are antigenically stable at physiological temperatures, it can be predicted that the VP3(178Q.L) VLPs will be immunogenic and generate neutralizing antibody titers similar to those observed with IPV.

Accordingly, it is demonstrated that N-form PV1 VLPs containing a VP3(178 Q.L) mutation were efficiently produced in HeLa cell-free reactions and are N-antigenically stable for 5 days at physiological temperatures. This is in contrast to the results observed with wildtype PV1 VLPs, which lost their N-antigenicity in a few hours. Remarkably, the stability of the N-form PV1(VP3 178 Q.L) VLPs was equivalent to that of type 1 poliovirus in IPV.

The approach used to make more stable N-form PV1 VLPs can be adapted to engineer stable N-form PV2 and PV3 VLPs. The design and characterization of stable PV1, PV2 and PV3 VLPs that are immunogenic and produce high-titer neutralizing antibodies.

Example 2: An Approach for Developing PV2 VLPs and PV3 VLPs Comprising Stabilizing Mutations Since the key elements of the proteolytic cleavage sites are highly conserved among the three serotypes of PV, especially for the $2A^{pro}$ cleavage site, PV2 and PV3 VLPs can be produced by replacing the P1 sequence of PV1 with P1 sequences of either PV2 or PV3. PV2 and PV3 capsid-coding sequences can be engineered into the PV1 translation expression construct (PV1 P1-2A-3CD) using subgenomic cDNA clones than contain either the PV2 or the PV3 capsid sequences. In these chimeric translation expression constructs, herein referred to as PV2 P1-2A-3CD and PV3 P1-2A-3CD for the PV2 and PV3 chimeric constructs respectively, the PC2 P1 or PV3 P1 coding sequences will replace the PV1 P1 coding sequence. Once constructed, the PV2 P1-2A-3CD and PV3 P1-2A-3CD expression RNAs can be used to synthesize VLPs for PV2 and PV3 as described in Example 1.

Based on an in silico analysis of the PV1 VP3(178Q.L) mutant, it appears that a hydrophobic cluster is created between leucine 178 in VP3 and its binding partners isoleucine 201 in VP1 and isoleucine 180 in VP3. These interactions may confer the increased thermal stability of the mutant VLPs (Table 1 and FIG. 8). The distances between the leucine and each of its hydrophobic binding partners are all less than 5 Å, supporting the idea that this van der Waals contact patch may significantly contribute to the observed increase in stability of the N-antigenic form of VP3(178Q.L) VLPs. The retention of the N-antigenicity of PV1 VP3 (178Q.L) VLPs at physiological temperatures, was consistent with that the preliminary in silico modeling at this site. In addition, the VP3(178Q.L) mutation was previously shown to inhibit the binding of soluble forms of the poliovirus receptor (Colston, E. and Racaniello, V, EMBO J. 13:5855-5862, 1994). This mutation was also shown to reduce the affinity of mutant virus for binding to cells by about 10-fold compared to wildtype virus. Even partial inhibition of binding to the poliovirus receptor protein, CD155, may also contribute to the antigenicity of this mutant VLP since binding of poliovirus to its receptor normally induces a conformation change in the virus capsid.

Thus, in silico modeling can be used to design similar mutations in PV2 and PV3 which will also confer increased stability of the N-antigenic form of the poliovirus capsid. An initial target from mutagenesis of PV2 a PV3 capsids is the VP3 178 position. Both PV2 and PV1 poliovirus share extensive similarities in the residues of the VP1-VP3 interface around the VP3 178 position. This amino acid is a conserved glutamine in all three polio serotypes. The almost identical positional arrangement of the residues in type 2 (FIG. 9) as compared to type 1 at the VP3 178 interface region is of particular interest as this would suggest a similar mutation of the glutamine to a leucine could also generate a PV2 VLP that exhibits increased stability of its N-antigenic form. The increased stability of the N-antigenic form with the VP3(178 Q.L) mutation is of particular interest as this area and some of the neighboring residues are also associated with the binding of the poliovirus receptor CD155 as noted above.

Increased variation from the PV1 VP3 178 residue environment is seen in PV3 (FIG. 10). In particular the isoleucine 180 and isoleucine 201 that are conserved between PV1 and PV2 are a threonine and leucine at those positions in PV3, respectively. A PV3 triple mutant of VP3(180T.V), VP3(178Q.L), and VP1(236D.V) could confer a similar increase in the stability of the PV3 capsid. The VP3(178Q.L) mutation can be tested alone or in combination with one of the other two mutations.

These wildtype and mutant PV2 and PV3 VLPs can be fractionated on a 15-30% sucrose gradient to determine if they sediment at 74S. An ELISA can be used to show that the PV2 and PV3 VLPs are in the N-antigenic form. For the PV2 and PV3 VLP ELISAs, the following commercially available antibodies can be used: (1) Anti-Polio component type II clone: 45 D5, Cat #HYB 300-05-02, ThermoFisher and (2) Anti-Polio component type III clone: 45 D5, Cat #HYB 300-05-02, ThermoFisher. These antibodies have been previously characterized by the CDC to detect the N-form PV2 and PV3 capsids, respectively. The N-form PV2 and PV3 VLPs can be visualized by electron microscopy for particle size, integrity and morphology, as described in Example 1.

Some Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, some embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A composition comprising poliovirus (PV) virus like particles (VLPs) comprising one or more stabilizing mutations, wherein the VLPs are thermostable in N-antigenic form, and wherein the one or more stabilizing mutations comprise:

VP3(178Q.L) in SEQ ID NO: 4, VP3(167V.D) in SEQ ID NO: 4, VP3(4V.C) in SEQ ID NO: 4, VP1(147N.C) in SEQ ID NO: 5, VP1(231A.V) in SEQ ID NO: 5, and/or VP2(201R.K) in SEQ ID NO: 3.

2. The composition of claim 1, wherein the poliovirus is poliovirus serotype 2 (PV2) or poliovirus serotype 3 (PV3).

3. The composition of claim 1, wherein the VLPs comprise proteins belonging to more than one poliovirus serotype.

4. The composition of claim 1, wherein the VLPs sediment at 74S on a 15-30% sucrose gradient.

5. The composition of claim 1, wherein the VLPs are 28-32 nm in diameter.

6. The composition of claim 1, wherein the VLPs are at a titer of 0.1-100 N-antigenic units/μl.

7. The composition of claim 2, wherein the poliovirus is poliovirus 2 (PV2), and wherein the one or more stabilizing mutations comprise a mutation corresponding to VP3 (178Q.L) in SEQ ID NO: 4.

8. The composition of claim 2, wherein the poliovirus is poliovirus 2 (PV2).

9. The composition of claim 2, wherein the poliovirus is poliovirus 3 (PV3), wherein the one or more stabilizing mutations comprise a mutation corresponding to VP3 (178Q.L) in SEQ ID NO: 4, and wherein the one or more stabilizing mutations further comprise VP3(180T.V) in SEQ ID NO: 4, and/or VP3(236D.V) in SEQ ID NO: 4.

10. The composition of claim 1, wherein the one or more stabilizing mutations are at the interface between one or more VP proteins in the VLP.

11. The composition of claim 1, wherein the one or more stabilizing mutations are at positions corresponding to 1-10 amino acids upstream of VP3(178Q) in SEQ ID NO: 4, or 1-10 amino acids downstream of VP3(178Q) in SEQ ID NO: 4.

12. The composition of claim 1, wherein the one or more stabilizing mutations are at positions of VP3 that interface with VP1.

13. The composition of claim 1, wherein the VLPs are thermostable in N-antigenic form for up to 8 h at 37° C., or 39° C.

14. A poliovirus vaccine comprising the composition of claim 1.

15. A composition comprising poliovirus (PV) virus like particles (VLPs) comprising one or more stabilizing mutations, wherein the VLPs are thermostable in N-antigenic form, and wherein the one or more stabilizing mutations comprise VP3(178Q.L) in SEQ ID NO: 4.

16. The composition of claim 15, wherein the one or more stabilizing mutations further comprise VP3(167V.D) in SEQ ID NO: 4, VP3(4V.C) in SEQ ID NO: 4, VP1(147N.C) in SEQ ID NO: 5, VP1(231A.V) in SEQ ID NO: 5, and/or VP2(201R.K) in SEQ ID NO: 3.

17. The composition of claim 16, wherein the poliovirus is poliovirus 2 (PV2) or poliovirus 3 (PV3).

18. A composition comprising poliovirus (PV) virus like particles (VLPs) comprising a stabilizing mutation, wherein the VLPs are thermostable in N-antigenic form, and wherein the stabilizing mutation consists of VP3(178Q.L) in SEQ ID NO: 4.

* * * * *

SEQUENCE LISTING

```
<160> NUMBER OF SEQ ID NOS: 9

<210> SEQ ID NO 1
<211> LENGTH: 340
<212> TYPE: PRT
<213> ORGANISM: Poliovirus Serotype 1 VP0

<400> SEQUENCE: 1

Gly Ala Gln Val Ser Ser Gln Lys Val Gly Ala His Glu Asn Ser Asn
1               5                   10                  15

Arg Ala Tyr Gly Gly Ser Thr Ile Asn Tyr Thr Thr Ile Asn Tyr Tyr
            20                  25                  30

Arg Asp Ser Ala Ser Asn Ala Ala Ser Lys Gln Asp Phe Ser Gln Asp
        35                  40                  45

Pro Ser Lys Phe Thr Glu Pro Ile Lys Asp Val Leu Ile Lys Thr Ala
    50                  55                  60
```

-continued

```
Pro Met Leu Asn Ser Pro Asn Ile Glu Ala Cys Gly Tyr Ser Asp Arg
65                  70                  75                  80

Val Leu Gln Leu Thr Leu Gly Asn Ser Thr Ile Thr Thr Gln Glu Ala
                85                  90                  95

Ala Asn Ser Val Val Ala Tyr Gly Arg Trp Pro Glu Tyr Leu Arg Asp
            100                 105                 110

Ser Glu Ala Asn Pro Val Asp Gln Pro Thr Glu Pro Asp Val Ala Ala
        115                 120                 125

Cys Arg Phe Tyr Thr Leu Asp Thr Val Ser Trp Thr Lys Glu Ser Arg
    130                 135                 140

Gly Trp Trp Trp Lys Leu Pro Asp Ala Leu Arg Asp Met Gly Leu Phe
145                 150                 155                 160

Gly Gln Asn Met Tyr Tyr His Tyr Leu Gly Arg Ser Gly Tyr Thr Val
                165                 170                 175

His Val Gln Cys Asn Ala Ser Lys Phe His Gln Gly Ala Leu Gly Val
            180                 185                 190

Phe Ala Val Pro Glu Met Cys Leu Ala Gly Asp Ser Asn Thr Thr Thr
        195                 200                 205

Met His Thr Ser Tyr Gln Asn Ala Asn Pro Gly Glu Lys Gly Gly Thr
    210                 215                 220

Phe Thr Gly Thr Phe Thr Pro Asp Asn Asn Gln Thr Ser Pro Ala Arg
225                 230                 235                 240

Arg Phe Cys Pro Val Asp Tyr Leu Leu Gly Asn Gly Thr Leu Leu Gly
                245                 250                 255

Asn Ala Phe Val Phe Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Val Lys His Asn Asn Trp Gly Ile Ala Ile Leu Pro Leu Ala Pro
    290                 295                 300

Leu Asn Phe Ala Ser Glu Ser Ser Pro Glu Ile Pro Ile Thr Leu Thr
305                 310                 315                 320

Ile Ala Pro Met Cys Cys Glu Phe Asn Gly Leu Arg Asn Ile Thr Leu
                325                 330                 335

Pro Arg Leu Gln
            340


<210> SEQ ID NO 2
<211> LENGTH: 68
<212> TYPE: PRT
<213> ORGANISM: Poliovirus Serotype 1 VP4

<400> SEQUENCE: 2

Gly Ala Gln Val Ser Ser Gln Lys Val Gly Ala His Glu Asn Ser Asn
1               5                   10                  15

Arg Ala Tyr Gly Gly Ser Thr Ile Asn Tyr Thr Thr Ile Asn Tyr Tyr
            20                  25                  30

Arg Asp Ser Ala Ser Asn Ala Ala Ser Lys Gln Asp Phe Ser Gln Asp
        35                  40                  45

Pro Ser Lys Phe Thr Glu Pro Ile Lys Asp Val Leu Ile Lys Thr Ala
    50                  55                  60

Pro Met Leu Asn
65


<210> SEQ ID NO 3
```

-continued

<211> LENGTH: 272
<212> TYPE: PRT
<213> ORGANISM: Poliovirus Serotype 1 VP2

<400> SEQUENCE: 3

Ser Pro Asn Ile Glu Ala Cys Gly Tyr Ser Asp Arg Val Leu Gln Leu
1 5 10 15

Thr Leu Gly Asn Ser Thr Ile Thr Thr Gln Glu Ala Ala Asn Ser Val
20 25 30

Val Ala Tyr Gly Arg Trp Pro Glu Tyr Leu Arg Asp Ser Glu Ala Asn
35 40 45

Pro Val Asp Gln Pro Thr Glu Pro Asp Val Ala Ala Cys Arg Phe Tyr
50 55 60

Thr Leu Asp Thr Val Ser Trp Thr Lys Glu Ser Arg Gly Trp Trp Trp
65 70 75 80

Lys Leu Pro Asp Ala Leu Arg Asp Met Gly Leu Phe Gly Gln Asn Met
85 90 95

Tyr Tyr His Tyr Leu Gly Arg Ser Gly Tyr Thr Val His Val Gln Cys
100 105 110

Asn Ala Ser Lys Phe His Gln Gly Ala Leu Gly Val Phe Ala Val Pro
115 120 125

Glu Met Cys Leu Ala Gly Asp Ser Asn Thr Thr Thr Met His Thr Ser
130 135 140

Tyr Gln Asn Ala Asn Pro Gly Glu Lys Gly Gly Thr Phe Thr Gly Thr
145 150 155 160

Phe Thr Pro Asp Asn Asn Gln Thr Ser Pro Ala Arg Arg Phe Cys Pro
165 170 175

Val Asp Tyr Leu Leu Gly Asn Gly Thr Leu Leu Gly Asn Ala Phe Val
180 185 190

Phe Pro His Gln Ile Ile Asn Leu Arg Thr Asn Asn Cys Ala Thr Leu
195 200 205

Val Leu Pro Tyr Val Asn Ser Leu Ser Ile Asp Ser Met Val Lys His
210 215 220

Asn Asn Trp Gly Ile Ala Ile Leu Pro Leu Ala Pro Leu Asn Phe Ala
225 230 235 240

Ser Glu Ser Ser Pro Glu Ile Pro Ile Thr Leu Thr Ile Ala Pro Met
245 250 255

Cys Cys Glu Phe Asn Gly Leu Arg Asn Ile Thr Leu Pro Arg Leu Gln
260 265 270

<210> SEQ ID NO 4
<211> LENGTH: 238
<212> TYPE: PRT
<213> ORGANISM: Poliovirus Serotype 1 VP3

<400> SEQUENCE: 4

Gly Leu Pro Val Met Asn Thr Pro Gly Ser Asn Gln Tyr Leu Thr Ala
1 5 10 15

Asp Asn Phe Gln Ser Pro Cys Ala Leu Pro Glu Phe Asp Val Thr Pro
20 25 30

Pro Ile Asp Ile Pro Gly Glu Val Lys Asn Met Met Glu Leu Ala Glu
35 40 45

Ile Asp Thr Met Ile Pro Phe Asp Leu Ser Ala Thr Lys Lys Asn Thr
50 55 60

Met Glu Met Tyr Arg Val Arg Leu Ser Asp Lys Pro His Thr Asp Asp
65 70 75 80

```
Pro Ile Leu Cys Leu Ser Leu Ser Pro Ala Ser Asp Pro Arg Leu Ser
                85                  90                  95

His Thr Met Leu Gly Glu Ile Leu Asn Tyr Tyr Thr His Trp Ala Gly
            100                 105                 110

Ser Leu Lys Phe Thr Phe Leu Phe Cys Gly Phe Met Met Ala Thr Gly
        115                 120                 125

Lys Leu Leu Val Ser Tyr Ala Pro Pro Gly Ala Asp Pro Pro Lys Lys
    130                 135                 140

Arg Lys Glu Ala Met Leu Gly Thr His Val Ile Trp Asp Ile Gly Leu
145                 150                 155                 160

Gln Ser Ser Cys Thr Met Val Val Pro Trp Ile Ser Asn Thr Thr Tyr
                165                 170                 175

Arg Gln Thr Ile Asp Asp Ser Phe Thr Glu Gly Gly Tyr Ile Ser Val
            180                 185                 190

Phe Tyr Gln Thr Arg Ile Val Val Pro Leu Ser Thr Pro Arg Glu Met
        195                 200                 205

Asp Ile Leu Gly Phe Val Ser Ala Cys Asn Asp Phe Ser Val Arg Leu
    210                 215                 220

Leu Arg Asp Thr Thr His Ile Glu Gln Lys Ala Leu Ala Gln
225                 230                 235


<210> SEQ ID NO 5
<211> LENGTH: 302
<212> TYPE: PRT
<213> ORGANISM: Poliovirus Serotype 1 VP1

<400> SEQUENCE: 5

Gly Leu Gly Gln Met Leu Glu Ser Met Ile Asp Asn Thr Val Arg Glu
1               5                   10                  15

Thr Val Gly Ala Ala Thr Ser Arg Asp Ala Leu Pro Asn Thr Glu Ala
            20                  25                  30

Ser Gly Pro Thr His Ser Lys Glu Ile Pro Ala Leu Thr Ala Val Glu
        35                  40                  45

Thr Gly Ala Thr Asn Pro Leu Val Pro Ser Asp Thr Val Gln Thr Arg
    50                  55                  60

His Val Val Gln His Arg Ser Arg Ser Glu Ser Ser Ile Glu Ser Phe
65                  70                  75                  80

Phe Ala Arg Gly Ala Cys Val Thr Ile Met Thr Val Asp Asn Pro Ala
                85                  90                  95

Ser Thr Thr Asn Lys Asp Lys Leu Phe Ala Val Trp Lys Ile Thr Tyr
            100                 105                 110

Lys Asp Thr Val Gln Leu Arg Arg Lys Leu Glu Phe Phe Thr Tyr Ser
        115                 120                 125

Arg Phe Asp Met Glu Leu Thr Phe Val Val Thr Ala Asn Phe Thr Glu
    130                 135                 140

Thr Asn Asn Gly His Ala Leu Asn Gln Val Tyr Gln Ile Met Tyr Val
145                 150                 155                 160

Pro Pro Gly Ala Pro Val Pro Glu Lys Trp Asp Asp Tyr Thr Trp Gln
                165                 170                 175

Thr Ser Ser Asn Pro Ser Ile Phe Tyr Thr Tyr Gly Thr Ala Pro Ala
            180                 185                 190

Arg Ile Ser Val Pro Tyr Val Gly Ile Ser Asn Ala Tyr Ser His Phe
        195                 200                 205

Tyr Asp Gly Phe Ser Lys Val Pro Leu Lys Asp Gln Ser Ala Ala Leu
```

-continued

```
    210                 215                 220

Gly Asp Ser Leu Tyr Gly Ala Ala Ser Leu Asn Asp Phe Gly Ile Leu
225                 230                 235                 240

Ala Val Arg Val Val Asn Asp His Asn Pro Thr Lys Val Thr Ser Lys
                245                 250                 255

Ile Arg Val Tyr Leu Lys Pro Lys His Ile Arg Val Trp Cys Pro Arg
            260                 265                 270

Pro Pro Arg Ala Val Ala Tyr Tyr Gly Pro Gly Val Asp Tyr Lys Asp
        275                 280                 285

Gly Thr Leu Thr Pro Leu Ser Thr Lys Asp Leu Thr Thr Tyr
    290                 295                 300


<210> SEQ ID NO 6
<211> LENGTH: 644
<212> TYPE: PRT
<213> ORGANISM: Poliovirus Serotype 1 3CD

<400> SEQUENCE: 6

Gly Pro Gly Phe Asp Tyr Ala Val Ala Met Ala Lys Arg Asn Ile Val
1               5                   10                  15

Thr Ala Thr Thr Ser Lys Gly Glu Phe Thr Met Leu Gly Val His Asp
            20                  25                  30

Asn Val Ala Ile Leu Pro Thr His Ala Ser Pro Gly Glu Ser Ile Val
        35                  40                  45

Ile Asp Gly Lys Glu Val Glu Ile Leu Asp Ala Lys Ala Leu Glu Asp
    50                  55                  60

Gln Ala Gly Thr Asn Leu Glu Ile Thr Ile Ile Thr Leu Lys Arg Asn
65                  70                  75                  80

Glu Lys Phe Arg Asp Ile Arg Pro His Ile Pro Thr Gln Ile Thr Glu
                85                  90                  95

Thr Asn Asp Gly Val Leu Ile Val Asn Thr Ser Lys Tyr Pro Asn Met
            100                 105                 110

Tyr Val Pro Val Gly Ala Val Thr Glu Gln Gly Tyr Leu Asn Leu Gly
        115                 120                 125

Gly Arg Gln Thr Ala Arg Thr Leu Met Tyr Asn Phe Pro Thr Arg Ala
    130                 135                 140

Gly Gln Cys Gly Gly Val Ile Thr Cys Thr Gly Lys Val Ile Gly Met
145                 150                 155                 160

His Val Gly Gly Asn Gly Ser His Gly Phe Ala Ala Ala Leu Lys Arg
                165                 170                 175

Ser Tyr Phe Thr Gln Ser Gln Gly Glu Ile Gln Trp Met Arg Pro Ser
            180                 185                 190

Lys Glu Val Gly Tyr Pro Ile Ile Asn Ala Pro Ser Lys Thr Lys Leu
        195                 200                 205

Glu Pro Ser Ala Phe His Tyr Val Phe Glu Gly Val Lys Glu Pro Ala
    210                 215                 220

Val Leu Thr Lys Asn Asp Pro Arg Leu Lys Thr Asp Phe Glu Glu Ala
225                 230                 235                 240

Ile Phe Ser Lys Tyr Val Gly Asn Lys Ile Thr Glu Val Asp Glu Tyr
                245                 250                 255

Met Lys Glu Ala Val Asp His Tyr Ala Gly Gln Leu Met Ser Leu Asp
            260                 265                 270

Ile Asn Thr Glu Gln Met Cys Leu Glu Asp Ala Met Tyr Gly Thr Asp
        275                 280                 285
```

-continued

Gly Leu Glu Ala Leu Asp Leu Ser Thr Ser Ala Gly Tyr Pro Tyr Val
290 295 300

Ala Met Gly Lys Lys Lys Arg Asp Ile Leu Asn Lys Gln Thr Arg Asp
305 310 315 320

Thr Lys Glu Met Gln Lys Leu Leu Asp Thr Tyr Gly Ile Asn Leu Pro
325 330 335

Leu Val Thr Tyr Val Lys Asp Glu Leu Arg Ser Lys Thr Lys Val Glu
340 345 350

Gln Gly Lys Ser Arg Leu Ile Glu Ala Ser Ser Leu Asn Asp Ser Val
355 360 365

Ala Met Arg Met Ala Phe Gly Asn Leu Tyr Ala Ala Phe His Lys Asn
370 375 380

Pro Gly Val Ile Thr Gly Ser Ala Val Gly Cys Asp Pro Asp Leu Phe
385 390 395 400

Trp Ser Lys Ile Pro Val Leu Met Glu Glu Lys Leu Phe Ala Phe Asp
405 410 415

Tyr Thr Gly Tyr Asp Ala Ser Leu Ser Pro Ala Trp Phe Glu Ala Leu
420 425 430

Lys Met Val Leu Glu Lys Ile Gly Phe Gly Asp Arg Val Asp Tyr Ile
435 440 445

Asp Tyr Leu Asn His Ser His His Leu Tyr Lys Asn Lys Thr Tyr Cys
450 455 460

Val Lys Gly Gly Met Pro Ser Gly Cys Ser Gly Thr Ser Ile Phe Asn
465 470 475 480

Ser Met Ile Asn Asn Leu Ile Ile Arg Thr Leu Leu Leu Lys Thr Tyr
485 490 495

Lys Gly Ile Asp Leu Asp His Leu Lys Met Ile Ala Tyr Gly Asp Asp
500 505 510

Val Ile Ala Ser Tyr Pro His Glu Val Asp Ala Ser Leu Leu Ala Gln
515 520 525

Ser Gly Lys Asp Tyr Gly Leu Thr Met Thr Pro Ala Asp Lys Ser Ala
530 535 540

Thr Phe Glu Thr Val Thr Trp Glu Asn Val Thr Phe Leu Lys Arg Phe
545 550 555 560

Phe Arg Ala Asp Glu Lys Tyr Pro Phe Leu Ile His Pro Val Met Pro
565 570 575

Met Lys Glu Ile His Glu Ser Ile Arg Trp Thr Lys Asp Pro Arg Asn
580 585 590

Thr Gln Asp His Val Arg Ser Leu Cys Leu Leu Ala Trp His Asn Gly
595 600 605

Glu Glu Glu Tyr Asn Lys Phe Leu Ala Lys Ile Arg Ser Val Pro Ile
610 615 620

Gly Arg Ala Leu Leu Leu Pro Glu Tyr Ser Thr Leu Tyr Arg Arg Trp
625 630 635 640

Leu Asp Ser Phe

<210> SEQ ID NO 7
<211> LENGTH: 182
<212> TYPE: PRT
<213> ORGANISM: Poliovirus Serotype 1 3C

<400> SEQUENCE: 7

Gly Pro Gly Phe Asp Tyr Ala Val Ala Met Ala Lys Arg Asn Ile Val
1 5 10 15

Thr Ala Thr Thr Ser Lys Gly Glu Phe Thr Met Leu Gly Val His Asp
20 25 30

Asn Val Ala Ile Leu Pro Thr His Ala Ser Pro Gly Glu Ser Ile Val
35 40 45

Ile Asp Gly Lys Glu Val Glu Ile Leu Asp Ala Lys Ala Leu Glu Asp
50 55 60

Gln Ala Gly Thr Asn Leu Glu Ile Thr Ile Ile Thr Leu Lys Arg Asn
65 70 75 80

Glu Lys Phe Arg Asp Ile Arg Pro His Ile Pro Thr Gln Ile Thr Glu
85 90 95

Thr Asn Asp Gly Val Leu Ile Val Asn Thr Ser Lys Tyr Pro Asn Met
100 105 110

Tyr Val Pro Val Gly Ala Val Thr Glu Gln Gly Tyr Leu Asn Leu Gly
115 120 125

Gly Arg Gln Thr Ala Arg Thr Leu Met Tyr Asn Phe Pro Thr Arg Ala
130 135 140

Gly Gln Cys Gly Gly Val Ile Thr Cys Thr Gly Lys Val Ile Gly Met
145 150 155 160

His Val Gly Gly Asn Gly Ser His Gly Phe Ala Ala Ala Leu Lys Arg
165 170 175

Ser Tyr Phe Thr Gln Ser
180

<210> SEQ ID NO 8
<211> LENGTH: 880
<212> TYPE: PRT
<213> ORGANISM: Poliovirus Serotype 1 P1

<400> SEQUENCE: 8

Gly Ala Gln Val Ser Ser Gln Lys Val Gly Ala His Glu Asn Ser Asn
1 5 10 15

Arg Ala Tyr Gly Gly Ser Thr Ile Asn Tyr Thr Thr Ile Asn Tyr Tyr
20 25 30

Arg Asp Ser Ala Ser Asn Ala Ala Ser Lys Gln Asp Phe Ser Gln Asp
35 40 45

Pro Ser Lys Phe Thr Glu Pro Ile Lys Asp Val Leu Ile Lys Thr Ala
50 55 60

Pro Met Leu Asn Ser Pro Asn Ile Glu Ala Cys Gly Tyr Ser Asp Arg
65 70 75 80

Val Leu Gln Leu Thr Leu Gly Asn Ser Thr Ile Thr Thr Gln Glu Ala
85 90 95

Ala Asn Ser Val Val Ala Tyr Gly Arg Trp Pro Glu Tyr Leu Arg Asp
100 105 110

Ser Glu Ala Asn Pro Val Asp Gln Pro Thr Glu Pro Asp Val Ala Ala
115 120 125

Cys Arg Phe Tyr Thr Leu Asp Thr Val Ser Trp Thr Lys Glu Ser Arg
130 135 140

Gly Trp Trp Trp Lys Leu Pro Asp Ala Leu Arg Asp Met Gly Leu Phe
145 150 155 160

Gly Gln Asn Met Tyr Tyr His Tyr Leu Gly Arg Ser Gly Tyr Thr Val
165 170 175

His Val Gln Cys Asn Ala Ser Lys Phe His Gln Gly Ala Leu Gly Val
180 185 190

Phe Ala Val Pro Glu Met Cys Leu Ala Gly Asp Ser Asn Thr Thr Thr
195 200 205

-continued

```
Met His Thr Ser Tyr Gln Asn Ala Asn Pro Gly Glu Lys Gly Gly Thr
    210                 215                 220

Phe Thr Gly Thr Phe Thr Pro Asp Asn Asn Gln Thr Ser Pro Ala Arg
225                 230                 235                 240

Arg Phe Cys Pro Val Asp Tyr Leu Leu Gly Asn Gly Thr Leu Leu Gly
                245                 250                 255

Asn Ala Phe Val Phe Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Val Lys His Asn Asn Trp Gly Ile Ala Ile Leu Pro Leu Ala Pro
    290                 295                 300

Leu Asn Phe Ala Ser Glu Ser Ser Pro Glu Ile Pro Ile Thr Leu Thr
305                 310                 315                 320

Ile Ala Pro Met Cys Cys Glu Phe Asn Gly Leu Arg Asn Ile Thr Leu
                325                 330                 335

Pro Arg Leu Gln Gly Leu Pro Val Met Asn Thr Pro Gly Ser Asn Gln
            340                 345                 350

Tyr Leu Thr Ala Asp Asn Phe Gln Ser Pro Cys Ala Leu Pro Glu Phe
        355                 360                 365

Asp Val Thr Pro Pro Ile Asp Ile Pro Gly Glu Val Lys Asn Met Met
    370                 375                 380

Glu Leu Ala Glu Ile Asp Thr Met Ile Pro Phe Asp Leu Ser Ala Thr
385                 390                 395                 400

Lys Lys Asn Thr Met Glu Met Tyr Arg Val Arg Leu Ser Asp Lys Pro
                405                 410                 415

His Thr Asp Asp Pro Ile Leu Cys Leu Ser Leu Ser Pro Ala Ser Asp
            420                 425                 430

Pro Arg Leu Ser His Thr Met Leu Gly Glu Ile Leu Asn Tyr Tyr Thr
        435                 440                 445

His Trp Ala Gly Ser Leu Lys Phe Thr Phe Leu Phe Cys Gly Phe Met
    450                 455                 460

Met Ala Thr Gly Lys Leu Leu Val Ser Tyr Ala Pro Pro Gly Ala Asp
465                 470                 475                 480

Pro Pro Lys Lys Arg Lys Glu Ala Met Leu Gly Thr His Val Ile Trp
                485                 490                 495

Asp Ile Gly Leu Gln Ser Ser Cys Thr Met Val Val Pro Trp Ile Ser
            500                 505                 510

Asn Thr Thr Tyr Arg Gln Thr Ile Asp Asp Ser Phe Thr Glu Gly Gly
        515                 520                 525

Tyr Ile Ser Val Phe Tyr Gln Thr Arg Ile Val Val Pro Leu Ser Thr
    530                 535                 540

Pro Arg Glu Met Asp Ile Leu Gly Phe Val Ser Ala Cys Asn Asp Phe
545                 550                 555                 560

Ser Val Arg Leu Leu Arg Asp Thr Thr His Ile Glu Gln Lys Ala Leu
                565                 570                 575

Ala Gln Gly Leu Gly Gln Met Leu Glu Ser Met Ile Asp Asn Thr Val
            580                 585                 590

Arg Glu Thr Val Gly Ala Ala Thr Ser Arg Asp Ala Leu Pro Asn Thr
        595                 600                 605

Glu Ala Ser Gly Pro Thr His Ser Lys Glu Ile Pro Ala Leu Thr Ala
    610                 615                 620
```

-continued

```
Val Glu Thr Gly Ala Thr Asn Pro Leu Val Pro Ser Asp Thr Val Gln
625                 630                 635                 640

Thr Arg His Val Val Gln His Arg Ser Arg Ser Glu Ser Ser Ile Glu
                645                 650                 655

Ser Phe Phe Ala Arg Gly Ala Cys Val Thr Ile Met Thr Val Asp Asn
            660                 665                 670

Pro Ala Ser Thr Thr Asn Lys Asp Lys Leu Phe Ala Val Trp Lys Ile
        675                 680                 685

Thr Tyr Lys Asp Thr Val Gln Leu Arg Arg Lys Leu Glu Phe Phe Thr
    690                 695                 700

Tyr Ser Arg Phe Asp Met Glu Leu Thr Phe Val Val Thr Ala Asn Phe
705                 710                 715                 720

Thr Glu Thr Asn Asn Gly His Ala Leu Asn Gln Val Tyr Gln Ile Met
                725                 730                 735

Tyr Val Pro Pro Gly Ala Pro Val Pro Glu Lys Trp Asp Asp Tyr Thr
            740                 745                 750

Trp Gln Thr Ser Ser Asn Pro Ser Ile Phe Tyr Thr Tyr Gly Thr Ala
        755                 760                 765

Pro Ala Arg Ile Ser Val Pro Tyr Val Gly Ile Ser Asn Ala Tyr Ser
    770                 775                 780

His Phe Tyr Asp Gly Phe Ser Lys Val Pro Leu Lys Asp Gln Ser Ala
785                 790                 795                 800

Ala Leu Gly Asp Ser Leu Tyr Gly Ala Ala Ser Leu Asn Asp Phe Gly
                805                 810                 815

Ile Leu Ala Val Arg Val Val Asn Asp His Asn Pro Thr Lys Val Thr
            820                 825                 830

Ser Lys Ile Arg Val Tyr Leu Lys Pro Lys His Ile Arg Val Trp Cys
        835                 840                 845

Pro Arg Pro Pro Arg Ala Val Ala Tyr Tyr Gly Pro Gly Val Asp Tyr
    850                 855                 860

Lys Asp Gly Thr Leu Thr Pro Leu Ser Thr Lys Asp Leu Thr Thr Tyr
865                 870                 875                 880


<210> SEQ ID NO 9
<211> LENGTH: 149
<212> TYPE: PRT
<213> ORGANISM: Poliovirus Serotype 1 2A

<400> SEQUENCE: 9

Gly Phe Gly His Gln Asn Lys Ala Val Tyr Thr Ala Gly Tyr Lys Ile
1               5                   10                  15

Cys Asn Tyr His Leu Ala Thr Gln Asp Asp Leu Gln Asn Ala Val Asn
            20                  25                  30

Val Met Trp Ser Arg Asp Leu Leu Val Thr Glu Ser Arg Ala Gln Gly
        35                  40                  45

Thr Asp Ser Ile Ala Arg Cys Asn Cys Asn Ala Gly Val Tyr Tyr Cys
    50                  55                  60

Glu Ser Arg Arg Lys Tyr Tyr Pro Val Ser Phe Val Gly Pro Thr Phe
65                  70                  75                  80

Gln Tyr Met Glu Ala Asn Asn Tyr Tyr Pro Ala Arg Tyr Gln Ser His
                85                  90                  95

Met Leu Ile Gly His Gly Phe Ala Ser Pro Gly Asp Cys Gly Gly Ile
            100                 105                 110

Leu Arg Cys His His Gly Val Ile Gly Ile Ile Thr Ala Gly Gly Glu
        115                 120                 125
```

-continued

```
Gly Leu Val Ala Phe Ser Asp Ile Arg Asp Leu Tyr Ala Tyr Glu Glu
    130                 135                 140

Glu Ala Met Glu Gln
145
```